US008440695B2

(12) United States Patent
Kastan et al.

(10) Patent No.: US 8,440,695 B2
(45) Date of Patent: May 14, 2013

(54) USE OF CHLOROQUINE TO TREAT METABOLIC SYNDROME

(75) Inventors: Michael B. Kastan, Cordova, TN (US); Clay F. Semenkovich, Ladue, MO (US); Jochen Schneider, St. Louis, MO (US)

(73) Assignees: St Jude Children's Research Hospital, Memphis, TN (US); The Washington University, St. Louis, MO (US)

( * ) Notice: Subject to any disclaimer, the term of this patent is extended or adjusted under 35 U.S.C. 154(b) by 335 days.

(21) Appl. No.: 12/093,198

(22) PCT Filed: Oct. 31, 2006

(86) PCT No.: PCT/US2006/060391
§ 371 (c)(1),
(2), (4) Date: May 30, 2008

(87) PCT Pub. No.: WO2007/059372
PCT Pub. Date: May 24, 2007

(65) Prior Publication Data
US 2008/0319010 A1 Dec. 25, 2008

Related U.S. Application Data

(60) Provisional application No. 60/736,192, filed on Nov. 9, 2005.

(51) Int. Cl.
*A61K 31/47* (2006.01)
(52) U.S. Cl.
USPC .......................................................... 514/313
(58) Field of Classification Search .................... 514/313
See application file for complete search history.

(56) References Cited

U.S. PATENT DOCUMENTS

| | | | |
|---|---|---|---|
| 2,233,970 A | 3/1941 | Andersag et al. |
| 2,635,940 A | 4/1953 | Fritze |
| 4,346,227 A | 8/1982 | Terahara et al. |
| 4,421,920 A | 12/1983 | Baudouin et al. |
| 4,431,807 A | 2/1984 | Strube et al. |
| 4,444,784 A | 4/1984 | Hoffman et al. |
| 4,839,177 A | 6/1989 | Colombo et al. |
| 4,857,522 A | 8/1989 | DiPietro et al. |
| 4,891,223 A | 1/1990 | Ambegaonkar et al. |
| 5,190,970 A | 3/1993 | Pan et al. |
| 5,316,765 A | 5/1994 | Folkers et al. |
| 5,397,574 A | 3/1995 | Chen |
| 5,399,358 A | 3/1995 | Baichwal et al. |
| 5,399,359 A | 3/1995 | Baichwal |
| 5,399,362 A | 3/1995 | Baichwal et al. |
| 5,419,917 A | 5/1995 | Chen et al. |
| 5,422,123 A | 6/1995 | Conte et al. |
| 5,456,921 A | 10/1995 | Mateescu et al. |
| 5,458,005 A | 10/1995 | Perelshteyn |
| 5,458,888 A | 10/1995 | Chen |
| 5,461,039 A | 10/1995 | Tschollar et al. |
| 5,464,633 A | 11/1995 | Conte et al. |
| 5,472,708 A | 12/1995 | Chen |
| 5,510,356 A | 4/1996 | Vennerstrom |
| 5,512,297 A | 4/1996 | Baichwal |
| 5,596,002 A | 1/1997 | Hofheinz et al. |
| 5,603,956 A | 2/1997 | Mateescu et al. |
| 5,624,938 A | 4/1997 | Pernis |
| 5,639,737 A | 6/1997 | Rubin |
| 5,639,761 A | 6/1997 | Francois et al. |
| 5,668,149 A | 9/1997 | Oroszlan et al. |
| 5,725,883 A | 3/1998 | Staniforth et al. |
| 5,736,557 A | 4/1998 | Hofheinz et al. |
| 5,773,025 A | 6/1998 | Baichwal |
| 5,824,638 A | 10/1998 | Burnside et al. |
| 5,834,023 A | 11/1998 | Chen |
| 5,837,379 A | 11/1998 | Chen et al. |
| 5,885,616 A | 3/1999 | Hsiao et al. |
| 5,897,876 A | 4/1999 | Rudnic et al. |
| 5,912,013 A | 6/1999 | Rudnic et al. |
| 5,916,595 A | 6/1999 | Chen et al. |
| 5,948,791 A | 9/1999 | Hofheinz et al. |
| 5,952,004 A | 9/1999 | Rudnic et al. |
| 5,968,983 A | 10/1999 | Kaesemeyer |
| 6,004,582 A | 12/1999 | Faour et al. |

(Continued)

FOREIGN PATENT DOCUMENTS

| | | |
|---|---|---|
| EP | 730663 | 9/1996 |
| GB | 2202846 | 10/1988 |
| WO | WO-84/02131 | 6/1984 |
| WO | WO 97/38709 | * 10/1997 |
| WO | WO-98/47491 | 10/1998 |

OTHER PUBLICATIONS

Irarrazabal CE, Liu JC, Burg MB, and Ferraris JD, "ATM, a DNA damage-inducible kinase, contributes to activation by high NaCl of the transcription factor TonEBP/OREBP," Proceedings of the National Academy of Sciences, Jun. 2004, 101(23), 8809-8814.*
Cleveland Clinic (http://my.clevelandclinic.org/disorders/Metabolic_Syndrome/hic_Metabolic_Syndrome.aspx) Feb. 9, 2007.*
Parker KL and Schimmer BP, Chapter 56 Pituitary Hormones and Their Hypothalamic Releasing Factors, "Goodman & Gilman's the Pharmacological Basis of Therapeutics, 10th ed." Hardman JG, Limbird LE, and Gilman AG, Eds., McGraw-Hill, 2001, 1541-1562 (pp. 1541, 1543, and 1545 provided).*
Shahrabani-Gargir L, Pandita TK, and Werner H, "Ataxia-telangiectasia mutated gene controls insulin-like growth factor I receptor gene expression in a deoxyribonucleic acid damage response pathway via mechanisms involving zinc-finger transcription factors Sp1 and WT1," Endocrinology, Dec. 2004, 145(12), 5679-5687 (Epub Sep. 2004).*
Wilkinson GR, Chapter 1 Pharmacokinetics—The Dynamics of Drug Absorption, Distribution, and Elimination, "Goodman & Gilman's the Pharmacological Basis of Therapeutics, 10th ed." Hardman JG, Limbird LE, and Gilman AG, Eds., McGraw-Hill, 2001, 3-30 (pp. 3, 5, and 6 provided).*

(Continued)

*Primary Examiner* — Paul Zarek
(74) *Attorney, Agent, or Firm* — Fish & Richardson P.C.

(57) ABSTRACT

The present invention provides methods and compositions for modulating certain metabolic processes and for treating a variety of disorders associated with metabolic syndrome, including insulin related disorders, ischemia, oxidative stress, atherosclerosis, hypertension, obesity, abnormal lipid metabolism, and stroke by administering an effective dose of a chloroquine compound. The invention also provides methods and compositions relating to administering an effective dose of a chloroquine compound in combination with at least a second pharmaceutically active ingredient or compound including an antihyperglycemic diabetes treatment, an antihypertensive agent, an antithrombotic agent, and/or an inhibitor of cholesterol synthesis or absorption.

29 Claims, No Drawings

U.S. PATENT DOCUMENTS

| | | | |
|---|---|---|---|
| 6,077,541 | A | 6/2000 | Chen et al. |
| 6,096,340 | A | 8/2000 | Chen et al. |
| 6,099,862 | A | 8/2000 | Chen et al. |
| 6,103,263 | A | 8/2000 | Lee et al. |
| 6,106,862 | A | 8/2000 | Chen et al. |
| 6,110,498 | A | 8/2000 | Rudnic et al. |
| 6,127,111 | A | 10/2000 | Braun et al. |
| 6,239,172 | B1 | 5/2001 | Kaesemeyer |
| 6,417,177 | B1 | 7/2002 | Nelson |
| 6,425,881 | B1 | 7/2002 | Kaesemeyer |
| 6,610,272 | B1 | 8/2003 | Cutie et al. |
| 6,734,197 | B2 | 5/2004 | Randazzo et al. |
| 6,756,408 | B2 | 6/2004 | Uretsky |
| 6,846,800 | B1 | 1/2005 | Johannsson et al. |
| 6,933,279 | B2 | 8/2005 | Fogelman et al. |
| 2003/0077661 | A1 | 4/2003 | Kastan et al. |
| 2005/0032834 | A1 | 2/2005 | Kastan et al. |
| 2005/0171140 | A1 | 8/2005 | O'Connor et al. |

OTHER PUBLICATIONS

Umesako et al., Atm heterozygous deficiency enhances development of mammary carcinomas in p53 heterozygous knockout mice, *Breast Cancer Research*, Dec. 2004, vol. 7, No. 1, pp. R164-R170.

UniProtKB/Swiss-ProtentryQ62388, http://www.ncbi.nlm.nih.gov, 5 pages.

Holtzman et al., Expression of human apolipoprotein E reduces amyloid-β deposition ina mouse model of Alzheimer's disease, *The Journal of Clinical Investigation*, Mar. 1999, vol. 103, No. 6, pp. R15-R21.

Yang etal., Participation of ATM in insulin signalling through phosphorylation of elF-4E binding protein 1, *Nature Cell Biology*, Dec. 2000, vol. 2, pp. 893-898.

Bakkenist et al., DNA damage activates ATM through intermolecular autophosphorylation and dimer dissociation, *Nature*, Jan. 2003, vol. 421, pp. 499-506.

Jochen G.Schneider et al., ATM-dependent suppression of stress signaling reduces vascular disease in metabolic syndrome, *Cell Metabolism*, Nov. 2006, No. 4: pp. 377-389.

Munro, et al., Effect of disease modifying agents on the lipid profiles of patients with rheumatoid arthritis, *Annals of the Rheumatic Diseases*, Feb. 1997, 56, pp. 374-377.

Vlijmen et al., Macrophage p53 Deficiency Leads to Enhanced Atherosclerosis in APOE*3- Leiden Transgenic Mice, *Circulation Research*, Apr. 2001; 88: pp. 780-786.

Powrie et al., Mode of action of chloroquine in patients with non-insulin-dependent diabetes mellitus, *American Physiological Society*, 1991, pp. E897-E904.

Rahman et al., The Cholesterol Lowering Effect of Antimalarial Drugs Is Enhanced in patients with Lupus Taking Corticosteroid Drugs, *The Journal of Rheumatology*, 1999; 26(2): pp. 325-330.

Wallace, The use of chloroquine and hydroxychloroquine for non-infectious conditions other than rheumatoid arthritis or lupus: a critical review, *Lupus* 1996, 5, Suppl 1: pp. S59-S64.

Semenkovich, Insulin resistance and atherosclerosis, *The Journal of Clinical Investigation*, Jul. 2006; vol. 116, No. 7, pp. 1813-1822.

Augustijns et al., Stereoselective Pharmacokinetic Properties of Chloroquine and De-Ethyl-Chloroquine in Humans, *Clin. Pharmacokinetics*, 1993; 24(3), pp. 259-263.

Augustijns et al., Stereoselective de-ethylation of chloroquine in rat liver microsomes *European Journal of Drug Metabolism and Pharmacokinetics*. 1999, vol. 24, No. 1, pp. 105-108.

Ducharme et al., Clinical Pharmacokinetics and Metabolism of Chloroquine, *Clinical Pharmacokinetcs and Pharmacokinetics*, Oct. 1996; (4), pp. 257-274.

Garber et al., Follow-up Study of Twenty-four Families with Li-Fraumeni Syndrome, *Cancer Research*, Nov. 1991, 51, pp. 6094-6097.

Olsen et al., Cancer in Patients with Ataxia-Telagiectasia and in their Relatives in the Nordic Countries, *Journal of the National Cancer Institute*, Jan. 2001; vol. 93, pp. 121-127.

"Physician's Desk Reference", Medical Economics Company, Inc. Montvale, N. J. (54th Edition) 2000; 2733-2735.

Coull et al., Anticoagulants and Antiplatelet Agents in Acute Ischemic Stroke: Report of the Joint Stroke Guideline Development Committee of the American Academy of Neurology and the American Stroke Association, *Stroke* 2002; 33, pp. 1934-1942.

Spring et al., Mice heterozygous for mutation in Atm, the gene involved in ataxia-telangiectasia, have heightened susceptibility to cancer, *Nature Genetics*,Sep. 2002, vol. 32, pp. 185-190.

Haffner et al., Hyperinsulinemia in Population at High Risk for Non-Insulin-Dependent Diabetes Mellitus, *The New England Journal of Medicine*, Jul. 1986; vol. 315, pp. 220-224.

Semenkovich et al., Effects of heterozygous lipoprotein lipase deficiency on diet-induced atheroscerosis in mice, *Journal of Lipid Research*, 1998; vol. 39, pp. 1141-1151.

Bernal-Mizrachi et al., Dexamethasone induction of hypertension and diabetes in PPAR-α dependent in LDL receptor-null mice, Aug. 2003; vol. 9, No. 8, pp. 1069-1075.

Tordjman et al., PPAR-α deficiency reduces insulin resistance and atherosclerosis in apoE-null mice, *The Journal of Clinical Investigation*, 2001, vol. 107, No. 8, pp. 1025-1034.

Weng et al., β3 integrin deficiency promotes atherosclerosis and pulmonary inflammation in high-fat-fed, hyperlipidemic mice, *Proc. National Academy of Science*, May 2003, vol. 100, No. 11, pp. 6730-6735.

Coleman et al., COOH-terminal Disruption of Lipoprotein Lipase in Mice is Lethal in Homozygotes, but Heterozygotes Have Elevated Triglycerides and Impaired Enzyme Activity, *The Journal of Biological Chemistry*, May 1995, vol. 270, No. 21, pp. 12518-12525.

Li et al., Skeletal muscle respiratory uncoupling prevents diet-induced obesity and insulin resistance in mice, *National Medicen*, Oct. 2000, vol. 6, No. 10, pp. 1115-1120.

Febbraio et al., Targeted disruption of the class B scavenger receptor CD36 protects against atherosclerotic lesion development in mice, *The Journal of Clinical Investigation*, Apr. 2000, vol. 105, No. 8 pp. 1049-1056.

Freireich et al., quantitative Comparison of Toxicity of Anticancer Agents in Mouse, Rat, Hamster, Dog, Monkey, and Man, *Cancer Chemotherapy Reports*, May 1966, vol. 50, No. 4, pp. 219-244.

The IDF Consensus Worldwide Definition of the Metabolic Syndrome, International Diabetes Federation (2006), 1-24.

American Association of Clinical Endocrinologists Medical Guidelines for Clinical Practice for Growth Hormone use in Adults and Children—2003 Update, AACE Growth Hormone Task Force, Endocrine Practice (2003), 9:65-76.

Moltch, Mark E., Clinical Manifestations of Acromegaly, Endocrinology and Metabolism Clinics of North America, Acromegaly (1992), 21(3):597-614.

Colao, Annamaria et al., Systemic Complications of Acromegaly: Epidemiology, Pathogenesis, and Management, Endocrine Reviews (2004), 25(1):102-152.

Melmed, Shlomo, Acromegaly pathogenesis and treatment, The Journal of Clinical Investigation (2009), 119(11):3189-3202.

Cornier, Marc-Andre et al., The Metabolic Syndrome, Endocrine Reviews (2008) 29(7) :777-822.

Shoelson, Steven E., Banking on ATM as a new target in metabolic syndrome, Cell Metabolism, (2006) 337-338.

Suckling, Keith, Drug discovery in the metabolic syndrome: context and some recent developments, Expert Opinion Ther. Targets (2007), 11(6):801-808.

Jackson, Stephen P. and Bartek, Jiri, The DNA-damage response in human biology and disease, Nature (2009), 461(22):1071-1078.

Borba, Eduardo F. et al., Longterm beneficial effect of chloroquine diphosphate on lipoprotein profile in lupus patients with and without steroid therapy, The Journal of Rheumatology, vol. 28(4), pp. 780-785, (2001).

Van Doornum, S. et al., Accelerated atherosclerosis: an extraarticular feature of rheumatoid arthritis?, Arthritis & Rheumatism, vol. 46(4), pp. 862-873, (2002).

\* cited by examiner

SEQUENCE LISTING

<160> NUMBER OF SEQ ID NOS: 18

<210> SEQ ID NO 1
<211> LENGTH: 3056
<212> TYPE: PRT
<213> ORGANISM: Homo sapiens

<400> SEQUENCE: 1

```
Met Ser Leu Val Leu Asn Asp Leu Leu Ile Cys Cys Arg Gln Leu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365
```

```
Ser Tyr Thr Thr Thr Gln Arg Glu Ser Ser Asp Tyr Ser Val Pro Cys
    370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
                405                 410                 415
Thr Gln Leu Ile Ser Lys Tyr Pro Ala Ser Leu Pro Asn Cys Glu Leu
            420                 425                 430
Ser Pro Leu Leu Met Ile Leu Ser Gln Leu Leu Pro Gln Gln Arg His
        435                 440                 445
Gly Glu Arg Thr Pro Tyr Val Leu Arg Cys Leu Thr Glu Val Ala Leu
    450                 455                 460
Cys Gln Asp Lys Arg Ser Asn Leu Glu Ser Ser Gln Lys Ser Asp Leu
465                 470                 475                 480
Leu Lys Leu Trp Asn Lys Ile Trp Cys Ile Thr Phe Arg Gly Ile Ser
                485                 490                 495
Ser Glu Gln Ile Gln Ala Glu Asn Phe Gly Leu Leu Gly Ala Ile Ile
            500                 505                 510
Gln Gly Ser Leu Val Glu Val Asp Arg Glu Phe Trp Lys Leu Phe Thr
        515                 520                 525
Gly Ser Ala Cys Arg Pro Ser Cys Pro Ala Val Cys Cys Leu Thr Leu
    530                 535                 540
Ala Leu Thr Thr Ser Ile Val Pro Gly Ala Val Lys Met Gly Ile Glu
545                 550                 555                 560
Gln Asn Met Cys Glu Val Asn Arg Ser Phe Ser Leu Lys Glu Ser Ile
                565                 570                 575
Met Lys Trp Leu Leu Phe Tyr Gln Leu Glu Gly Asp Leu Glu Asn Ser
            580                 585                 590
Thr Glu Val Pro Pro Ile Leu His Ser Asn Phe Pro His Leu Val Leu
        595                 600                 605
Glu Lys Ile Leu Val Ser Leu Thr Met Lys Asn Cys Lys Ala Ala Met
    610                 615                 620
Asn Phe Phe Gln Ser Val Pro Glu Cys Glu His His Gln Lys Asp Lys
625                 630                 635                 640
Glu Glu Leu Ser Phe Ser Glu Val Glu Leu Phe Leu Gln Thr Thr
                645                 650                 655
Phe Asp Lys Met Asp Phe Leu Thr Ile Val Arg Glu Cys Gly Ile Glu
            660                 665                 670
Lys His Gln Ser Ser Ile Gly Phe Ser Val His Gln Asn Leu Lys Glu
        675                 680                 685
Ser Leu Asp Arg Cys Leu Leu Gly Leu Ser Glu Gln Leu Leu Asn Asn
    690                 695                 700
Tyr Ser Ser Glu Ile Thr Asn Ser Glu Thr Leu Val Arg Cys Ser Arg
705                 710                 715                 720
Leu Leu Val Gly Val Leu Gly Cys Tyr Cys Tyr Met Gly Val Ile Ala
                725                 730                 735
Glu Glu Glu Ala Tyr Lys Ser Glu Leu Phe Gln Lys Ala Asn Ser Leu
            740                 745                 750
Met Gln Cys Ala Gly Glu Ser Ile Thr Leu Phe Lys Asn Lys Thr Asn
        755                 760                 765
Glu Glu Phe Arg Ile Gly Ser Leu Arg Asn Met Met Gln Leu Cys Thr
    770                 775                 780
Arg Cys Leu Ser Asn Cys Thr Lys Lys Ser Pro Asn Lys Ile Ala Ser
```

```
            785                 790                 795                 800
Gly Phe Phe Leu Arg Leu Leu Thr Ser Lys Leu Met Asn Asp Ile Ala
                805                 810                 815
Asp Ile Cys Lys Ser Leu Ala Ser Phe Ile Lys Lys Pro Phe Asp Arg
                820                 825                 830
Gly Glu Val Glu Ser Met Glu Asp Asp Thr Asn Gly Asn Leu Met Glu
                835                 840                 845
Val Glu Asp Gln Ser Ser Met Asn Leu Phe Asn Asp Tyr Pro Asp Ser
            850                 855                 860
Ser Val Ser Asp Ala Asn Glu Pro Gly Glu Ser Gln Ser Thr Ile Gly
865                 870                 875                 880
Ala Ile Asn Pro Leu Ala Glu Glu Tyr Leu Ser Lys Gln Asp Leu Leu
                885                 890                 895
Phe Leu Asp Met Leu Lys Phe Leu Cys Leu Cys Val Thr Thr Ala Gln
                900                 905                 910
Thr Asn Thr Val Ser Phe Arg Ala Ala Asp Ile Arg Arg Lys Leu Leu
                915                 920                 925
Met Leu Ile Asp Ser Ser Thr Leu Glu Pro Thr Lys Ser Leu His Leu
            930                 935                 940
His Met Tyr Leu Met Leu Leu Lys Glu Leu Pro Gly Glu Glu Tyr Pro
945                 950                 955                 960
Leu Pro Met Glu Asp Val Leu Glu Leu Leu Lys Pro Leu Ser Asn Val
                965                 970                 975
Cys Ser Leu Tyr Arg Arg Asp Gln Asp Val Cys Lys Thr Ile Leu Asn
                980                 985                 990
His Val Leu His Val Val Lys Asn  Leu Gly Gln Ser Asn  Met Asp Ser
            995                 1000                1005
Glu Asn  Thr Arg Asp Ala Gln  Gly Gln Phe Leu Thr  Val Ile Gly
    1010                1015                1020
Ala Phe Trp His Leu Thr Lys  Glu Arg Lys Tyr Ile  Phe Ser Val
    1025                1030                1035
Arg Met  Ala Leu Val Asn Cys  Leu Lys Thr Leu Leu  Glu Ala Asp
    1040                1045                1050
Pro Tyr  Ser Lys Trp Ala Ile  Leu Asn Val Met Gly  Lys Asp Phe
    1055                1060                1065
Pro Val  Asn Glu Val Phe Thr  Gln Phe Leu Ala Asp  Asn His His
    1070                1075                1080
Gln Val  Arg Met Leu Ala Ala  Glu Ser Ile Asn Arg  Leu Phe Gln
    1085                1090                1095
Asp Thr  Lys Gly Asp Ser Ser  Arg Leu Leu Lys Ala  Leu Pro Leu
    1100                1105                1110
Lys Leu  Gln Gln Thr Ala Phe  Glu Asn Ala Tyr Leu  Lys Ala Gln
    1115                1120                1125
Glu Gly  Met Arg Glu Met Ser  His Ser Ala Glu Asn  Pro Glu Thr
    1130                1135                1140
Leu Asp  Glu Ile Tyr Asn Arg  Lys Ser Val Leu Leu  Thr Leu Ile
    1145                1150                1155
Ala Val  Val Leu Ser Cys Ser  Pro Ile Cys Glu Lys  Gln Ala Leu
    1160                1165                1170
Phe Ala  Leu Cys Lys Ser Val  Lys Glu Asn Gly Leu  Glu Pro His
    1175                1180                1185
Leu Val  Lys Lys Val Leu Glu  Lys Val Ser Glu Thr  Phe Gly Tyr
    1190                1195                1200
```

-continued

```
Arg Arg Leu Glu Asp Phe Met Ala Ser His Leu Asp Tyr Leu Val
1205                1210                1215

Leu Glu Trp Leu Asn Leu Gln Asp Thr Glu Tyr Asn Leu Ser Ser
1220                1225                1230

Phe Pro Phe Ile Leu Leu Asn Tyr Thr Asn Ile Glu Asp Phe Tyr
1235                1240                1245

Arg Ser Cys Tyr Lys Val Leu Ile Pro His Leu Val Ile Arg Ser
1250                1255                1260

His Phe Asp Glu Val Lys Ser Ile Ala Asn Gln Ile Gln Glu Asp
1265                1270                1275

Trp Lys Ser Leu Leu Thr Asp Cys Phe Pro Lys Ile Leu Val Asn
1280                1285                1290

Ile Leu Pro Tyr Phe Ala Tyr Glu Gly Thr Arg Asp Ser Gly Met
1295                1300                1305

Ala Gln Gln Arg Glu Thr Ala Thr Lys Val Tyr Asp Met Leu Lys
1310                1315                1320

Ser Glu Asn Leu Leu Gly Lys Gln Ile Asp His Leu Phe Ile Ser
1325                1330                1335

Asn Leu Pro Glu Ile Val Val Glu Leu Leu Met Thr Leu His Glu
1340                1345                1350

Pro Ala Asn Ser Ser Ala Ser Gln Ser Thr Asp Leu Cys Asp Phe
1355                1360                1365

Ser Gly Asp Leu Asp Pro Ala Pro Asn Pro Pro His Phe Pro Ser
1370                1375                1380

His Val Ile Lys Ala Thr Phe Ala Tyr Ile Ser Asn Cys His Lys
1385                1390                1395

Thr Lys Leu Lys Ser Ile Leu Glu Ile Leu Ser Lys Ser Pro Asp
1400                1405                1410

Ser Tyr Gln Lys Ile Leu Leu Ala Ile Cys Glu Gln Ala Ala Glu
1415                1420                1425

Thr Asn Asn Val Tyr Lys Lys His Arg Ile Leu Lys Ile Tyr His
1430                1435                1440

Leu Phe Val Ser Leu Leu Lys Asp Ile Lys Ser Gly Leu Gly
1445                1450                1455

Gly Ala Trp Ala Phe Val Leu Arg Asp Val Ile Tyr Thr Leu Ile
1460                1465                1470

His Tyr Ile Asn Gln Arg Pro Ser Cys Ile Met Asp Val Ser Leu
1475                1480                1485

Arg Ser Phe Ser Leu Cys Cys Asp Leu Leu Ser Gln Val Cys Gln
1490                1495                1500

Thr Ala Val Thr Tyr Cys Lys Asp Ala Leu Glu Asn His Leu His
1505                1510                1515

Val Ile Val Gly Thr Leu Ile Pro Leu Val Tyr Glu Gln Val Glu
1520                1525                1530

Val Gln Lys Gln Val Leu Asp Leu Leu Lys Tyr Leu Val Ile Asp
1535                1540                1545

Asn Lys Asp Asn Glu Asn Leu Tyr Ile Thr Ile Lys Leu Leu Asp
1550                1555                1560

Pro Phe Pro Asp His Val Val Phe Lys Asp Leu Arg Ile Thr Gln
1565                1570                1575

Gln Lys Ile Lys Tyr Ser Arg Gly Pro Phe Ser Leu Leu Glu Glu
1580                1585                1590

Ile Asn His Phe Leu Ser Val Ser Val Tyr Asp Ala Leu Pro Leu
1595                1600                1605
```

Thr Arg Leu Glu Gly Leu Lys Asp Leu Arg Arg Gln Leu Glu Leu
1610                1615                1620

His Lys Asp Gln Met Val Asp Ile Met Arg Ala Ser Gln Asp Asn
1625                1630                1635

Pro Gln Asp Gly Ile Met Val Lys Leu Val Val Asn Leu Leu Gln
1640                1645                1650

Leu Ser Lys Met Ala Ile Asn His Thr Gly Glu Lys Glu Val Leu
1655                1660                1665

Glu Ala Val Gly Ser Cys Leu Gly Glu Val Gly Pro Ile Asp Phe
1670                1675                1680

Ser Thr Ile Ala Ile Gln His Ser Lys Asp Ala Ser Tyr Thr Lys
1685                1690                1695

Ala Leu Lys Leu Phe Glu Asp Lys Glu Leu Gln Trp Thr Phe Ile
1700                1705                1710

Met Leu Thr Tyr Leu Asn Asn Thr Leu Val Glu Asp Cys Val Lys
1715                1720                1725

Val Arg Ser Ala Ala Val Thr Cys Leu Lys Asn Ile Leu Ala Thr
1730                1735                1740

Lys Thr Gly His Ser Phe Trp Glu Ile Tyr Lys Met Thr Thr Asp
1745                1750                1755

Pro Met Leu Ala Tyr Leu Gln Pro Phe Arg Thr Ser Arg Lys Lys
1760                1765                1770

Phe Leu Glu Val Pro Arg Phe Asp Lys Glu Asn Pro Phe Glu Gly
1775                1780                1785

Leu Asp Asp Ile Asn Leu Trp Ile Pro Leu Ser Glu Asn His Asp
1790                1795                1800

Ile Trp Ile Lys Thr Leu Thr Cys Ala Phe Leu Asp Ser Gly Gly
1805                1810                1815

Thr Lys Cys Glu Ile Leu Gln Leu Leu Lys Pro Met Cys Glu Val
1820                1825                1830

Lys Thr Asp Phe Cys Gln Thr Val Leu Pro Tyr Leu Ile His Asp
1835                1840                1845

Ile Leu Leu Gln Asp Thr Asn Glu Ser Trp Arg Asn Leu Leu Ser
1850                1855                1860

Thr His Val Gln Gly Phe Phe Thr Ser Cys Leu Arg His Phe Ser
1865                1870                1875

Gln Thr Ser Arg Ser Thr Thr Pro Ala Asn Leu Asp Ser Glu Ser
1880                1885                1890

Glu His Phe Phe Arg Cys Cys Leu Asp Lys Lys Ser Gln Arg Thr
1895                1900                1905

Met Leu Ala Val Val Asp Tyr Met Arg Arg Gln Lys Arg Pro Ser
1910                1915                1920

Ser Gly Thr Ile Phe Asn Asp Ala Phe Trp Leu Asp Leu Asn Tyr
1925                1930                1935

Leu Glu Val Ala Lys Val Ala Gln Ser Cys Ala Ala His Phe Thr
1940                1945                1950

Ala Leu Leu Tyr Ala Glu Ile Tyr Ala Asp Lys Lys Ser Met Asp
1955                1960                1965

Asp Gln Glu Lys Arg Ser Leu Ala Phe Glu Glu Gly Ser Gln Ser
1970                1975                1980

Thr Thr Ile Ser Ser Leu Glu Lys Ser Lys Glu Glu Thr Gly
1985                1990                1995

Ile Ser Leu Gln Asp Leu Leu Leu Glu Ile Tyr Arg Ser Ile Gly

```
                2000                2005                2010

Glu Pro Asp Ser Leu Tyr Gly Cys Gly Gly Lys Met Leu Gln
    2015                2020                2025

Pro Ile Thr Arg Leu Arg Thr Tyr Glu His Glu Ala Met Trp Gly
    2030                2035                2040

Lys Ala Leu Val Thr Tyr Asp Leu Glu Thr Ala Ile Pro Ser Ser
    2045                2050                2055

Thr Arg Gln Ala Gly Ile Ile Gln Ala Leu Gln Asn Leu Gly Leu
    2060                2065                2070

Cys His Ile Leu Ser Val Tyr Leu Lys Gly Leu Asp Tyr Glu Asn
    2075                2080                2085

Lys Asp Trp Cys Pro Glu Leu Glu Glu Leu His Tyr Gln Ala Ala
    2090                2095                2100

Trp Arg Asn Met Gln Trp Asp His Cys Thr Ser Val Ser Lys Glu
    2105                2110                2115

Val Glu Gly Thr Ser Tyr His Glu Ser Leu Tyr Asn Ala Leu Gln
    2120                2125                2130

Ser Leu Arg Asp Arg Glu Phe Ser Thr Phe Tyr Glu Ser Leu Lys
    2135                2140                2145

Tyr Ala Arg Val Lys Glu Val Glu Glu Met Cys Lys Arg Ser Leu
    2150                2155                2160

Glu Ser Val Tyr Ser Leu Tyr Pro Thr Leu Ser Arg Leu Gln Ala
    2165                2170                2175

Ile Gly Glu Leu Glu Ser Ile Gly Glu Leu Phe Ser Arg Ser Val
    2180                2185                2190

Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile
    2210                2215                2220

Met Ala Leu Arg Thr Val Ile Leu Glu Ile Leu Met Glu Lys Glu
    2225                2230                2235

Met Asp Asn Ser Gln Arg Glu Cys Ile Lys Asp Ile Leu Thr Lys
    2240                2245                2250

His Leu Val Glu Leu Ser Ile Leu Ala Arg Thr Phe Lys Asn Thr
    2255                2260                2265

Gln Leu Pro Glu Arg Ala Ile Phe Gln Ile Lys Gln Tyr Asn Ser
    2270                2275                2280

Val Ser Cys Gly Val Ser Glu Trp Gln Leu Glu Glu Ala Gln Val
    2285                2290                2295

Phe Trp Ala Lys Lys Glu Gln Ser Leu Ala Leu Ser Ile Leu Lys
    2300                2305                2310

Gln Met Ile Lys Lys Leu Asp Ala Ser Cys Ala Ala Asn Asn Pro
    2315                2320                2325

Ser Leu Lys Leu Thr Tyr Thr Glu Cys Leu Arg Val Cys Gly Asn
    2330                2335                2340

Trp Leu Ala Glu Thr Cys Leu Glu Asn Pro Ala Val Ile Met Gln
    2345                2350                2355

Thr Tyr Leu Glu Lys Ala Val Glu Val Ala Gly Asn Tyr Asp Gly
    2360                2365                2370

Glu Ser Ser Asp Glu Leu Arg Asn Gly Lys Met Lys Ala Phe Leu
    2375                2380                2385

Ser Leu Ala Arg Phe Ser Asp Thr Gln Tyr Gln Arg Ile Glu Asn
    2390                2395                2400
```

-continued

```
Tyr Met Lys Ser Ser Glu Phe Glu Asn Lys Gln Ala Leu Leu Lys
    2405                2410                2415

Arg Ala Lys Glu Glu Val Gly Leu Leu Arg Glu His Lys Ile Gln
    2420                2425                2430

Thr Asn Arg Tyr Thr Val Lys Val Gln Arg Glu Leu Glu Leu Asp
    2435                2440                2445

Glu Leu Ala Leu Arg Ala Leu Lys Glu Asp Arg Lys Arg Phe Leu
    2450                2455                2460

Cys Lys Ala Val Glu Asn Tyr Ile Asn Cys Leu Leu Ser Gly Glu
    2465                2470                2475

Glu His Asp Met Trp Val Phe Arg Leu Cys Ser Leu Trp Leu Glu
    2480                2485                2490

Asn Ser Gly Val Ser Glu Val Asn Gly Met Met Lys Arg Asp Gly
    2495                2500                2505

Met Lys Ile Pro Thr Tyr Lys Phe Leu Pro Leu Met Tyr Gln Leu
    2510                2515                2520

Ala Ala Arg Met Gly Thr Lys Met Met Gly Gly Leu Gly Phe His
    2525                2530                2535

Glu Val Leu Asn Asn Leu Ile Ser Arg Ile Ser Met Asp His Pro
    2540                2545                2550

His His Thr Leu Phe Ile Ile Leu Ala Leu Ala Asn Ala Asn Arg
    2555                2560                2565

Asp Glu Phe Leu Thr Lys Pro Glu Val Ala Arg Arg Ser Arg Ile
    2570                2575                2580

Thr Lys Asn Val Pro Lys Gln Ser Ser Gln Leu Asp Glu Asp Arg
    2585                2590                2595

Thr Glu Ala Ala Asn Arg Ile Ile Cys Thr Ile Arg Ser Arg Arg
    2600                2605                2610

Pro Gln Met Val Arg Ser Val Glu Ala Leu Cys Asp Ala Tyr Ile
    2615                2620                2625

Ile Leu Ala Asn Leu Asp Ala Thr Gln Trp Lys Thr Gln Arg Lys
    2630                2635                2640

Gly Ile Asn Ile Pro Ala Asp Gln Pro Ile Thr Lys Leu Lys Asn
    2645                2650                2655

Leu Glu Asp Val Val Pro Thr Met Glu Ile Lys Val Asp His
    2660                2665                2670

Thr Gly Glu Tyr Gly Asn Leu Val Thr Ile Gln Ser Phe Lys Ala
    2675                2680                2685

Glu Phe Arg Leu Ala Gly Gly Val Asn Leu Pro Lys Ile Ile Asp
    2690                2695                2700

Cys Val Gly Ser Asp Gly Lys Glu Arg Arg Gln Leu Val Lys Gly
    2705                2710                2715

Arg Asp Asp Leu Arg Gln Asp Ala Val Met Gln Gln Val Phe Gln
    2720                2725                2730

Met Cys Asn Thr Leu Leu Gln Arg Asn Thr Glu Thr Arg Lys Arg
    2735                2740                2745

Lys Leu Thr Ile Cys Thr Tyr Lys Val Val Pro Leu Ser Gln Arg
    2750                2755                2760

Ser Gly Val Leu Glu Trp Cys Thr Gly Thr Val Pro Ile Gly Glu
    2765                2770                2775

Phe Leu Val Asn Asn Glu Asp Gly Ala His Lys Arg Tyr Arg Pro
    2780                2785                2790

Asn Asp Phe Ser Ala Phe Gln Cys Gln Lys Lys Met Met Glu Val
    2795                2800                2805
```

| | | | | | | | | | |
|---|---|---|---|---|---|---|---|---|---|
| Gln | Lys | Lys | Ser | Phe | Glu | Glu | Lys | Tyr | Glu | Val | Phe | Met | Asp | Val |
| | 2810 | | | | 2815 | | | | 2820 | | | | | |

Gln Lys Lys Ser Phe Glu Glu Lys Tyr Glu Val Phe Met Asp Val
    2810                2815                2820

Cys Gln Asn Phe Gln Pro Val Phe Arg Tyr Phe Cys Met Glu Lys
2825                2830                2835

Phe Leu Asp Pro Ala Ile Trp Phe Glu Lys Arg Leu Ala Tyr Thr
2840                2845                2850

Arg Ser Val Ala Thr Ser Ser Ile Val Gly Tyr Ile Leu Gly Leu
2855                2860                2865

Gly Asp Arg His Val Gln Asn Ile Leu Ile Asn Glu Gln Ser Ala
2870                2875                2880

Glu Leu Val His Ile Asp Leu Gly Val Ala Phe Glu Gln Gly Lys
2885                2890                2895

Ile Leu Pro Thr Pro Glu Thr Val Pro Phe Arg Leu Thr Arg Asp
2900                2905                2910

Ile Val Asp Gly Met Gly Ile Thr Gly Val Glu Gly Val Phe Arg
2915                2920                2925

Arg Cys Cys Glu Lys Thr Met Glu Val Met Arg Asn Ser Gln Glu
2930                2935                2940

Thr Leu Leu Thr Ile Val Glu Val Leu Leu Tyr Asp Pro Leu Phe
2945                2950                2955

Asp Trp Thr Met Asn Pro Leu Lys Ala Leu Tyr Leu Gln Gln Arg
2960                2965                2970

Pro Glu Asp Glu Thr Glu Leu His Pro Thr Leu Asn Ala Asp Asp
2975                2980                2985

Gln Glu Cys Lys Arg Asn Leu Ser Asp Ile Asp Gln Ser Phe Asp
2990                2995                3000

Lys Val Ala Glu Arg Val Leu Met Arg Leu Gln Glu Lys Leu Lys
3005                3010                3015

Gly Val Glu Glu Gly Thr Val Leu Ser Val Gly Gly Gln Val Asn
3020                3025                3030

Leu Leu Ile Gln Gln Ala Ile Asp Pro Lys Asn Leu Ser Arg Leu
3035                3040                3045

Phe Pro Gly Trp Lys Ala Trp Val
3050                3055

<210> SEQ ID NO 2
<211> LENGTH: 620
<212> TYPE: DNA
<213> ORGANISM: Homo sapiens

<400> SEQUENCE: 2

```
gcgagaggag tcgggatctg cgctgcagcc accgccgcgg ttgatactac tttgaccttc      60
cgagtgcagt ggtaggggcg cggaggcaac gcagcggctt ctgcgctggg aaattcagtc     120
gtgtgcgacc cagtctgtcc tctccccaga ccgccaatct catgcacccc tccagagtgg     180
cccttgactc ctccctctcc tcactccatc tttcctggcc tctctccggg tgcttagcgg     240
acttggccaa taacctcctc cttttaaacg ccctgaattg aaccctgcct cctgcgcatc     300
ctcttttttgt gtcaccttag ggttcagatt taactacgcg acttgactag tcatcttttg     360
atctctctct cgtatttagt acttttagtc agcgagcatt tattgatatt caacttcag      420
cctcgcggtt aagagcttgg gctctggaat catacggctg gaattggaat tctgtcagtc     480
gtgtggccgc tctctactgt cttgtgaaga taagtgagat aatcttgacc tgtggtgagc     540
actcgtgagc gttagctgct gtatttacca ggtacagata agacaactac agtggatgat     600
```

```
aatgtatgtg gtgatagggg                                              620

<210> SEQ ID NO 3
<211> LENGTH: 30
<212> TYPE: DNA
<213> ORGANISM: artificial
<220> FEATURE:
<223> OTHER INFORMATION: primer

<400> SEQUENCE: 3
aagatgctgt catgcagcag gtcttccaga                                    30

<210> SEQ ID NO 4
<211> LENGTH: 30
<212> TYPE: DNA
<213> ORGANISM: artificial
<220> FEATURE:
<223> OTHER INFORMATION: primer

<400> SEQUENCE: 4
aattctctag agctcgctga tcagcctcga                                    30

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
ttgtccaacc tgagagtggc aatccatagc                                    30

<210> SEQ ID NO 6
<211> LENGTH: 25
<212> TYPE: DNA
<213> ORGANISM: artificial
<220> FEATURE:
<223> OTHER INFORMATION: primer

<400> SEQUENCE: 6
gtgctagact catggtttaa gattt                                         25

<210> SEQ ID NO 7
<211> LENGTH: 21
<212> TYPE: DNA
<213> ORGANISM: artificial
<220> FEATURE:
<223> OTHER INFORMATION: primer

<400> SEQUENCE: 7
cagtcccaca tcaggcttga g                                             21

<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8
ggactgcacg gatgacctta g                                             21

<210> SEQ ID NO 9
<211> LENGTH: 23
<212> TYPE: DNA
<213> ORGANISM: artificial
<220> FEATURE:
```

```
<223> OTHER INFORMATION: primer
<220> FEATURE:
<221> NAME/KEY: misc_feature
<222> LOCATION: (1)..(1)
<223> OTHER INFORMATION: 5' carboxyfluorescein label
<220> FEATURE:
<221> NAME/KEY: misc_feature
<222> LOCATION: (23)..(23)
<223> OTHER INFORMATION: 3' carboxytetramethylrhodamine label
<220> FEATURE:
<221> NAME/KEY: misc_feature
<222> LOCATION: (28)..(28)
<223> OTHER INFORMATION: 3' carboxytetramethylrhodamine label

<400> SEQUENCE: 9
ccttcaagtc agccagcccc ctg                                              23

<210> SEQ ID NO 10
<211> LENGTH: 24
<212> TYPE: DNA
<213> ORGANISM: artificial
<220> FEATURE:
<223> OTHER INFORMATION: primer

<400> SEQUENCE: 10 ttcactttc tgggactgag aatg                                              24

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
gccactgtgc cgtacagaga                                                  20

<210> SEQ ID NO 12
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(18)
<223> OTHER INFORMATION: 5' carboxyfluorescein label and 3'
      carboxytetramethylrhodamine label

<400> SEQUENCE: 12
tccagccagg atgcaaca                                                    18

<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13
```

```
gcctcgtgag catgaccaat                                                    20

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
gcagaggaag acgatgaagc a                                                  21

<210> SEQ ID NO 15
<211> LENGTH: 23
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(23)
<223> OTHER INFORMATION: 5' carboxyfluorescein label and 3' Biotin
      label

<400> SEQUENCE: 15
ctccgacctc ttcatcctcg gcg                                                23

<210> SEQ ID NO 16
<211> LENGTH: 19
<212> TYPE: DNA
<213> ORGANISM: artificial
<220> FEATURE:
<223> OTHER INFORMATION: primer

<400> SEQUENCE: 16
aagcgaaact ggcggaaac                                                     19

<210> SEQ ID NO 17
<211> LENGTH: 17
<212> TYPE: DNA
<213> ORGANISM: artificial
<220> FEATURE:
<223> OTHER INFORMATION: primer

<400> SEQUENCE: 17
gatctggccc ttgaacc                                                       17

<210> SEQ ID NO 18
<211> LENGTH: 24
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (1)..(24)
<223> OTHER INFORMATION: 5' HEX label and 3' Biotin label

<400> SEQUENCE: 18
cagaggcatt gacaacaggg tgcg                                               24
```

USE OF CHLOROQUINE TO TREAT METABOLIC SYNDROME

CROSS-REFERENCE TO PRIOR APPLICATION

This is a U.S. National Phase Application under 35 U.S.C. §371 of International Patent Application No. PCT/US2006/060391 filed Oct. 31, 2006, which claims the benefit of U.S. Provisional Pat. Application No. 60/736,192 filed Nov. 9, 2005, both of which are incorporated by reference herein. The International application was published in English on May 24, 2007 as WO 2007/059372 A2 under PCT Article 21(2).

CROSS REFERENCE TO RELATED APPLICATIONS

The present application claims the benefit under 35 U.S.C. 119(e), of U.S. Provisional Application 60/736,192, filed Nov. 9, 2005, which is hereby incorporated herein by reference in its entirety.

STATEMENT AS TO RIGHTS TO INVENTIONS MADE UNDER FEDERALLY SPONSORED RESEARCH OR DEVELOPMENT

This invention was made in part in the course of research sponsored by the National Institutes of Health (NIH Grant Nos. P50 HL083762, CA71387, CA21765, HL58427, AG20091, ES05777, and HL57278) as well as the Clinical Nutrition Research Unit (DK56341), the Diabetes Research and Training Center (DK20579). The U.S. government may have certain rights in this invention.

FIELD OF THE INVENTION

The present invention relates generally to methods and compositions for modulating certain metabolic processes. The invention further relates to treating a variety of symptoms associated with metabolic syndrome, including insulin related disorders, ischemia, oxidative stress, atherosclerosis, hypertension, obesity, abnormal lipid metabolism, and stroke by administering an effective dose of a chloroquine compound. In particular, the invention relates to increasing ATM activity in a mammal suffering from metabolic syndrome by administering an effective dose of a chloroquine compound.

BACKGROUND OF THE INVENTION

It is estimated that between 20-25% of American adults (about 47 million) have metabolic syndrome, a complex condition associated with an increased risk of vascular disease. Metabolic syndrome is also known as Syndrome X, metabolic syndrome X, insulin resistance syndrome, or Reaven's syndrome, after Dr. Gerald M. Reaven, who first described the disorder. Metabolic syndrome is generally believed to be a combination of disorders that affect a large number of people in a clustered fashion. The symptoms and features of the syndrome include at least three of the following conditions: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity). Insulin resistance is typical of metabolic syndrome and leads to several of its features, including glucose intolerance, dyslipidemia, and hypertension. Obesity is commonly associated with the syndrome as is increased abdominal girth, highlighting the fact that abnormal lipid metabolism likely contributes to the underlying pathophysiology of metabolic syndrome.

Metabolic syndrome was codified in the United States with the publication of the National Cholesterol Education Program Adult Treatment Panel III (ATP III) guidelines in 2001. On a physiologic basis, insulin resistance appears to be responsible for the syndrome. However, insulin resistance can be defined in a myriad of different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation, all of which have been implicated in the cardiovascular disease associated with metabolic syndrome. At least at present, there is no obvious molecular mechanism causing the syndrome, probably because the condition represents a failure of one or more of the many compensatory mechanisms that are activated in response to energy excess and the accumulation of fat.

According to ATP III, the diagnosis of metabolic syndrome requires the presence of three or more of the following: elevated fasting triglycerides (greater than or equal to 150 mg/dl), low HDL cholesterol (less than 50 mg/dl in women, less than 40 mg/dl in men), hypertension (blood pressure greater than or equal to 130/85 mm Hg), increased waist circumference (due to excess visceral adiposity, greater than 35 inches in women, greater than 40 inches in men) and elevated fasting glucose (greater than or equal to 100 mg/dl). The presence of three components is not a perfect predictor of insulin resistance, and the World Health Organization has established somewhat different criteria that include microalbuminuria (i.e., slightly elevated albumin excretion in the urine), and some groups modify the ATP III criteria to include a body mass index (BMI) of greater than or equal to 30 kg/$M^2$ and abnormal nonfasting glucose and lipid values. Regardless of the definition, the syndrome identifies a group of individuals at increased risk for vascular disease. In an analysis of the Third National Health and Nutrition Examination Survey (NHANES III) participants over the age of 50 with metabolic syndrome showed a coronary heart disease prevalence exceeding that of diabetes. NHANES II data indicate total mortality as well as death from coronary heart disease and cardiovascular disease are increased in adults with metabolic syndrome.

Individuals at risk for metabolic syndrome include those who exhibit central obesity with increased abdominal girth (due to excess visceral adiposity) of about more than 35 inches in women and more than 40 inches in men. Individuals at risk for metabolic syndrome also include those that have a BMI greater than or equal to 30 kg/$M^2$ and may also have abnormal levels of nonfasting glucose, lipids, and blood pressure.

Oxidative Stress, Metabolic Syndrome, and Vascular Disease

Reductionist systems, animal models and studies in humans are consistent with a role for reactive oxygen species in the development of vascular dysfunction. Chronic inflammation is one source of reactive oxygen species and an emerging body of evidence implicates inflammation and oxidative stress in vascular disease associated with the metabolic syndrome. CRP (C reactive protein), a circulating marker of inflammation, is higher in those with more components of the metabolic syndrome, and elevated CRP levels may be predictive of vascular disease events in women with the syndrome. Cytokines associated with insulin resistance, such as IL-6 and TNFα, also increase with obesity. Obesity promotes the accumulation of macrophages and an induction of an inflammatory pattern of gene expression in adipose tissue. Inhibition of oxidative stress pathways decreases reactive oxygen species in adipose tissue and improves metabolic syndrome in obese mouse models. Obesity increases expression of monocyte-chemoattractant protein-1, a proatherogenic molecule that also promotes insulin resistance.

JNK and the Metabolic Syndrome

While oxidative stress can affect multiple potential molecular mediators of the metabolic syndrome, c-Jun N-terminal kinase (JNK) may be particularly important. JNK, a member of the mitogen activated protein kinase superfamily of signaling molecules, is activated by stressors that include reactive oxygen species, fatty acids, and inflammatory cytokines. Activated JNK phosphorylates cJun, which in combination with cFos constitutes the AP-1 transcription factor complex. Several lines of evidence link JNK activity to features of the metabolic syndrome. JNK activity is increased by endoplasmic reticulum stress caused by obesity. There are three known JNK genes and multiple isoforms. JNK1 and 2 are widely distributed, while JNK3 expression is more limited. Mice deficient in JNK1 are protected from obesity and insulin resistance. Expression of wild type JNK in liver decreases insulin sensitivity and overexpression of a dominant negative JNK in liver increases insulin sensitivity in obese mice. JNK decreases the expression of adiponectin, which has insulin sensitizing effects, in adipocyte cell lines. Treatment of animals with a cell-permeable inhibitor of JNK enhances insulin sensitivity. At least part of the mechanism underlying the JNK effect is understood since JNK has been shown to interfere with insulin signaling by phosphorylating serine residue 307 on insulin receptor substrate 1 (IRS1). Pharmacologic inhibition of JNK activity and genetic JNK2 deficiency in apoE null mice decreases atherosclerosis, in part due to decreased activity of scavenger receptor A in the absence of JNK-dependent phosphorylation.

ATM and Stress Responses

Ataxia telangiectasia (AT) is an autosomal recessive disorder presenting in early childhood that is characterized by progressive cerebellar ataxia, skin and eye telangiectasias, a predisposition to malignancies (especially lymphomas), and immune deficiency. AT patients also manifest impaired growth, accelerated aging, and other signs of insulin resistance including glucose intolerance. The likely mechanism of AT was provided when the single gene responsible for this disease, ATM (Ataxia Telangiectasia Mutated) was identified and found to be a member of the phosphoinositol-3 kinase family. ATM was subsequently shown to be important for insulin signaling leading to translation initiation by Yang and Kastan in Nature Cell Bio., 2000, 2: 893-898. The frequency of ATM heterozygotes may be as high as 2% in the general population, and a study of these ATM carriers (405 grandparents of AT children) reported an increased risk of death from ischemic heart disease.

The primary function of ATM is to respond to DNA damage, much of which is caused by reactive oxygen species. After genotoxic stress, ATM initiates pathways that interfere with cell cycle progression, permitting DNA to be repaired before errors are propagated through replication. ATM is recognized to be important for restoring homeostasis in response to oxidative stress. Levels of manganese superoxide dismutase, catalase, and thioredoxin reflective of increased oxidative stress are present in cerebellae from ATM null mice. ATM resides at sites in the cytoplasm as well as the nucleus and co-localizes with catalase in peroxisomes; increased lipid peroxidation and decreased catalase has been detected in AT-deficient cells. Markers of oxidative stress are increased in both AT heterozygotes and homozygotes. Activation of JNK and the AP-1 pathway is present in the brains of ATM-deficient mice. Self-renewal of hematopoietic stem cells requires the inhibition of reactive oxygen species generation by ATM.

p53 and Atherosclerosis

How ATM modulates responses to oxidative stress is unknown but it is reasonable to assume that p53 is involved. The tumor suppressor p53 responds to DNA damage by inducing an increasingly complex series of events, including apoptosis and cell cycle arrest (which appear to be transcription-dependent), as well as control of DNA repair and recombination (which may be transcription-independent). In response to stress, activated ATM phosphorylates p53 and MDM2, which leads to an increase in p53 protein levels and activity. While a role for ATM in atherosclerosis has not been firmly established, several studies suggest that p53 may be involved in vascular disease. p53 (and MDM2) are present in human atherosclerotic lesions. In rabbits, diet-induced atherosclerosis is associated with oxidation-induced DNA damage and the induction of p53 in the vasculature. In the apoE null model, p53$^{-/-}$ mice have increased atherosclerosis associated with accelerated cell proliferation without an effect on apoptosis. The p53 effect appears to be mediated in part by macrophages, since the transplantation of p53 null bone marrow in both apoE*3-Leiden mice (an animal model for human-like atherosclerosis described by van Vlijmen et al., Circ Res., 2001, 88(8):780-6) as well as LDL receptor null mice results in more atherosclerosis. Recent evidence suggests that the anti-atherosclerotic effect of p53 in dietary models may be complex, promoting apoptosis in macrophages and preventing apoptosis in smooth muscle cells. The protective effect may be limited to diet-induced atherosclerosis models. Using a plaque-rupture model involving phenylephrine administration, one group reported that adenoviral-mediated overexpression of p53 in smooth muscle cells increased apoptosis and destabilized lesions. Another growth suppressor, p27 (a cyclin-dependent kinase inhibitor), has been shown to decrease diet-induced atherosclerosis by decreasing macrophage proliferation, but p21 (a different member of the same cyclin-dependent kinase inhibitor family) increases atherosclerosis. In short, recent studies have shown that ATM is an important activator of p53, and p53 is likely to have anti-atherogenic effects in the vasculature.

ATM and the Antimalarial Drug Chloroquine

Inactive ATM exists as a dimer in cells. In response to stress, ATM phosphorylates itself, a modification that does not affect the intrinsic kinase activity of the molecule, but instead dissociates the dimer and allows substrates access to the kinase domain of the molecule. This phosphorylation, representing ATM activation, occurs at serine 1981 of ATM and is sensitive to cellular stress. Low dose irradiation producing as few as four strand breaks in the entire genome and experiments using manipulated mammalian cells following induction of only two well-defined DNA strand breaks have been shown to cause ATM phosphorylation. Thus, it is believed that ATM activation does not require physical contact with DNA. Instead, since strand breaks alter chromatin structure, ATM is probably capable of sensing subtle changes in chromatin structure. Chromatin structure can be altered without inducing DNA strand breaks by several manipulations including exposure to mildly hypotonic media, inhibitors of histone deacetylase, and exposure to the antimalarial drug chloroquine.

Chloroquine

Chloroquine is a DNA intercalating agent that functions as a mild topoisomerase II inhibitor. Chloroquine is used to prevent and treat malaria, a red blood cell infection with plasmodium species of protozoa transmitted by the bite of a mosquito, and to treat parasitic conditions such as liver disease caused by other protozoa (tiny one-celled animals).

Chloroquine and related aminoquinolines have also found use in the treatment of other chronic inflammatory diseases. Antimalarials were first described as treatments for rheumatologic disease in 1894, and the class gained acceptance for use in inflammatory conditions following a 1951 report in the Lancet. Chloroquine and related aminoquinolines have been shown to be effective for treating systemic lupus erythematosus (SLE) and rheumatoid arthritis (RA). These anti-inflammatory effects have led to their use as prophylaxis for deep venous thrombosis and treatment of sarcoidosis.

Chloroquine and Metabolism

Effects of chloroquine on insulin sensitivity were reported in 1984, when high dose chloroquine (1000 mg/day) was used in a patient to successfully reverse severe insulin resistance thought to be due to accelerated degradation of insulin. Subsequent studies confirmed a modest effect of glucose lowering that was proportional to the degree of insulin resistance, i.e., there was essentially no effect in non-diabetic subjects and the greatest effect was seen in those who were most insulin resistant, when administering high dose chloroquine. Chloroquine has been reported to increase the affinity of the insulin receptor and increase insulin secretion by isolated islets, both of which may reflect a global increase in insulin signaling. There is also a report of a hyperinsulinemic-euglycemic clamp study in patients with type 2 diabetes that demonstrated that administering high dose chloroquine (1000 mg/day) for three days modestly decreased insulin resistance in peripheral tissues without affecting endogenous glucose production (Powrie et al., Am. J. Physiol., 1991, 260:897-904). Rahman et al. (J. Rheumatol., 1999, 26(2): 325-30), reported that antimalarials lower total cholesterol in patients also receiving steroids and may minimize steroid induced hypercholesterolemia in patients with systemic lupus erythematosus. Munro et al. (Ann. Rheum. Dis., 1997, 56:374-377) reported that for a test group of 100 rheumatoid arthritis patients, the group treated with oral hydroxychloroquine had a significant overall improvement in their lipid profile. Wallace (Lupus, 1996, 5 Suppl 1:S59-64) concluded that chloroquines are safe and effective as a therapy for selected patients having any one of the following disorders: porphyria cutanea tarda, cutaneous sarcoidosis, cutaneous manifestations of dermatomyositis, hyperlipidemias, and thromboembolic prophylaxis for patients with antiphospholipid antibodies.

Insulin resistance is widely held to explain the association between the metabolic syndrome and vascular disease. However, insulin resistance may not directly cause atherosclerosis (Semenkovich, 2006, J. Clin. Invest. 116:1813-1822). Insulin resistance is not related to vascular lesions after correcting for glucose tolerance. Pioglitazone, an insulin sensitizer, does not decrease cardiovascular events in patients with insulin resistance. Studies directly addressing the role of macrophage insulin resistance in atherosclerosis are conflicting. As opposed to representing a unique entity, the metabolic syndrome may simply reflect the cumulative contribution of its components to atherosclerotic risk.

Historically, chloroquine has been used with caution because it can cause retinal toxicity. There are numerous reports addressing chloroquine toxicity that can be summarized as follows: reports that retinopathy is rare and the drug can be taken for years without toxicity; hydroxychloroquine, a less effective anti-inflammatory agent, can also cause retinopathy, although the risk is lower than with chloroquine; retinopathy risk is dose-dependent with the lowest cumulative dose associated with retinopathy being 125 grams (several groups have shown no effects despite cumulative doses of 300 grams); and doses of about 250 mg per day or 3.5 mg/kg per day are considered safe for chronic treatment.

Presently there is no one treatment for the combination of symptoms that make up metabolic syndrome. Thus, there is a need for an effective, safe treatment for the combination of disorders associated with metabolic syndrome. The present invention provides novel methods and compositions comprising low doses of a chloroquine compound to modulate ATM activity and to alleviate or prevent the numerous symptoms of metabolic syndrome. Compounds and methods of the present invention may also be utilized in combination with one or more other treatments such as antihyperglycemic diabetes treatment, an antihypertensive agent, an antithrombotic agent, and/or an inhibitor of cholesterol synthesis or absorption to augment these treatments.

SUMMARY OF THE INVENTION

The present invention provides methods of treating metabolic syndrome as well as methods of prophylaxis for metabolic syndrome and related disorders.

The invention also encompasses methods for treating metabolic syndrome by administering an effective amount of a chloroquine compound to a mammal in need of such treatment. In certain embodiments, the mammal is a human. The invention also includes a method for increasing Ataxia-Telangiectasia Mutated (ATM) protein kinase activity in a mammal with metabolic syndrome by administering an effective amount of a chloroquine compound to a mammal in need of such treatment. The invention includes the method where the mammal with metabolic syndrome exhibits improvement in symptoms associated with metabolic syndrome when compared to symptoms prior to administering the effective amount of a chloroquine compound.

In certain methods the metabolic syndrome comprises at least three symptoms selected from the group consisting of elevated fasting triglycerides (greater than or equal to 150 mg/dl), low HDL cholesterol (less than 50 mg/dl in women, less than 40 mg/dl in men), hypertension (blood pressure greater than or equal to 130/85 mm Hg), increased waist circumference (greater than 35 inches in women, greater than 40 inches in men) and elevated fasting glucose (greater than or equal to 100 mg/dl).

The methods also comprise administering to a subject at risk of metabolic syndrome, an effective amount of a chloroquine compound. Individuals at risk for metabolic syndrome include those who exhibit central obesity with increased abdominal girth of about more than 35 inches in women and about more than 40 inches in men. Individuals at risk for metabolic syndrome also include those that have a BMI greater than or equal to 30 kg/M$^2$ and may also have abnormal levels of fasting glucose, lipids and blood pressure.

In some methods, there is an additional step of determining presence of a genetic variation in an ATM gene of the subject at risk of the metabolic syndrome.

In some methods, the subject/mammal is free of diseases of the immune system, infectious diseases, and neurological diseases. In some methods, the subject is free of psoriasis, malaria, protozoal infections, Epstein Barr virus infection, Alzheimer's disease, Parkinson's disease, lupus erythematosus, rheumatism, hypercalcemia, multiple sclerosis, and migraine.

In some methods, the chloroquine is administered intravenously. In some methods, the chloroquine is administered orally.

In some methods, the chloroquine compound is selected from the group consisting of chloroquine, chloroquine phosphate, hydroxychloroquine, chloroquine diphosphate, chloroquine sulphate, hydroxychloroquine sulphate, or enantiomers, derivatives, analogs, metabolites, pharmaceutically acceptable salts, and mixtures thereof. Optionally, the chloroquine compound is chloroquine, chloroquine phosphate, hydroxychloroquine, or chloroquine diphosphate, or mixtures of any of these compounds. In certain methods the compound is chloroquine or hydroxychloroquine.

In some methods, the chloroquine compound is a mixture of isomers. In some methods the chloroquine compound is an essentially pure (+) isomer. In some methods the chloroquine compound is an essentially pure (−) isomer.

In some methods, the chloroquine compound has a systemic effect. In some methods, the amount of chloroquine compound administered is at least about 0.1 mg/kg per day. In some methods, the amount of chloroquine ranges from about 0.6 mg/kg/day to about 3.0 mg/kg/day. In some methods, the amount of chloroquine ranges from about 0.8 mg/kg/day to about 1.2 mg/kg/day. In some methods, the amount of the compound administered ranges from about 3.5 mg/kg to about 7 mg/kg per week. In some methods, the amount of the compound administered ranges from about 0.1 mg/kg/day to about 0.2 mg/kg/day. In some methods, the amount of the compound administered is about 80 mg/day. In some methods, the amount of the compound administered ranges from about 0.1 mg/kg to about 9 mg/kg once a week.

In some methods, the cumulative amount of the compound administered is less than about 30 grams (cumulative dose). In some methods, the cumulative amount of the compound administered is less than about 100 grams.

In some methods, the chloroquine compound is administered more than once a week. In some methods the chloroquine compound is administered daily. In some methods, the chloroquine compound is administered once a month. In some methods, the chloroquine compound is formulated in a sustained release formulation. In some methods, the patient is human.

The invention also provides methods and compositions relating to administering an effective dose of a chloroquine compound in combination with at least a second pharmaceutically active ingredient or compound. This second pharmaceutically active compound may include any of the treatments including an antihyperglycemic diabetes treatment, an antihypertensive agent, an antithrombotic agent, and an inhibitor of cholesterol synthesis or absorption.

An embodiment of the invention includes a composition for treating metabolic syndrome comprising an effective amount of a chloroquine compound and an effective amount of at least a second pharmaceutically active ingredient.

Another embodiment of the invention includes a pharmaceutical composition which comprises an amount of chloroquine effective to increase Ataxia-Telangiectasia Mutated (ATM) protein kinase activity in a mammal with metabolic syndrome and a pharmaceutically acceptable carrier.

A further embodiment of the invention includes a pharmaceutical composition which comprises an effective amount of chloroquine for increasing Ataxia-Telangiectasia Mutated (ATM) protein kinase activity in a mammal with metabolic syndrome, an effective amount of a second pharmaceutically active ingredient, and a pharmaceutically acceptable carrier. The pharmaceutical composition may include a second pharmaceutically active ingredient that is an antihyperglycemic diabetes treatment, an antihypertensive agent, an antithrombotic agent, and an inhibitor of cholesterol synthesis or absorption.

In certain embodiments the antihypertensive agent includes any of the following agents: an angiotensin converting enzyme inhibitor (ACE inhibitor), an angiotensin receptor blocker (ARB), a beta-blocker, and a calcium channel blocker. In certain embodiments the beta blocker includes any of the following agents: propranolol, atenolol, esmolol, metoprolol, labetalol, talinolol, timolol, carvedilol and acebutolol. In certain embodiments the calcium channel blocker includes any of the following agents: nifedipine, verapamil, diltiazem, and nimodipine. In certain embodiments the inhibitor of cholesterol synthesis includes any of the following agents: an inhibitor of HMG CoA reductase, squalene epoxidase, squalene synthetase, cholesterol sulfate, and phosphate synthetase.

In certain embodiments the inhibitor of HMG CoA reductase includes any of the following agents: atorvastatin, cerivastatin, simvastatin, lovastatin, pravastatin, compactin, fluvastatin, mevastatin, fluindostatin, and dalvastatin, cholesterol sulfate, cholesterol phosphate, 25-OH or 26-OH cholesterol, and oxygenated sterols.

In certain embodiments the antihyperglycemic diabetes treatment includes any of the following agents: insulin, an insulin analog, actos (pioglitazone), avandia (rosiglitazone), a sulfonylurea, tolbutamide, abiguanide-type medication/agent, phentolamine, and tolazemide.

In certain embodiments the antithrombotic agent includes any of the following agents: unfractionated heparin, low molecular weight (LMW) heparin, heparinoid, aspirin, ticlopidine, clopidogrel, dipyridamole, hirudin, and glycoprotein IIb/IIIa antagonists.

Embodiments of the present invention include a pharmaceutical composition comprising about 1 mg to about 140 mg of a chloroquine compound and a pharmaceutically acceptable carrier.

A further embodiment of the present invention includes a pharmaceutical composition comprising about 80 mg of a chloroquine compound and a pharmaceutically acceptable carrier. In certain embodiments the chloroquine compound is at least one compound selected from chloroquine, chloroquine phosphate, hydroxychloroquine, chloroquine diphosphate, chloroquine sulphate, hydroxychloroquine sulphate, or enantiomers, derivatives, analogs, metabolites, pharmaceutically acceptable salts, or mixtures thereof. In additional embodiments, the compound may be any compound selected from chloroquine, chloroquine phosphate, hydroxychloroquine, chloroquine diphosphate, or mixtures thereof. In a preferred embodiment, the compound is chloroquine. In yet further embodiments the compound is hydroxychloroquine.

In additional embodiments the chloroquine compound may be an essentially pure (+) isomer, an essentially pure (−) isomer, or a mixture of isomers.

In yet additional embodiments, the invention is directed to use of an effective amount of any of the aforementioned chloroquine compounds or compositions in the manufacture of a medicament to increase Ataxia-Telangiectasia Mutated (ATM) protein kinase activity in a mammal with metabolic syndrome, including for conditions associated with metabolic syndrome such as elevated fasting triglycerides, low HDL cholesterol, hypertension, increased weight circumference, elevated fasting glucose, or any combinations thereof.

In yet additional embodiments, the invention is directed to use of any of the aforementioned chloroquine compounds or compositions in the manufacture of a medicament for the therapeutic and/or prophylactic treatment of metabolic syndrome, including for treating conditions associated with metabolic syndrome such as elevated fasting triglycerides, low HDL cholesterol, hypertension, increased weight circumference, elevated fasting glucose, or any combinations thereof.

In yet additional embodiments, the invention is directed to use of any of the aforementioned chloroquine compounds or compositions in the manufacture of a medicament for the prophylaxis of metabolic syndrome, including for preventing symptoms or conditions associated with metabolic syndrome such as elevated fasting triglycerides, low HDL cholesterol, hypertension, increased weight circumference, elevated fasting glucose, or any combinations thereof.

In yet additional embodiments, the invention is directed to use of any of the aforementioned chloroquine compounds or compositions in combination with an effective amount of at least a second pharmaceutically active ingredient in the manufacture of a medicament for the therapeutic and/or prophylactic treatment of metabolic syndrome, including for treating conditions associated with metabolic syndrome such as elevated fasting triglycerides, low HDL cholesterol, hypertension, increased weight circumference, elevated fasting glucose, or any combinations thereof.

DETAILED DESCRIPTION

The present invention provides methods, compositions, and kits for the prevention, prophylaxis and/or treatment of metabolic syndrome and its related disorders. The disorders associated with metabolic syndrome include insulin resistance, glucose intolerance, hypertension, obesity, abnormal lipid metabolism (e.g. dyslipidemia), central adiposity, oxidative stress and its many manifestations including, stroke, ischemia, and atherosclerosis. Although there is some overlap between these disorders (for example, atherosclerosis is a common cause of ischemia and ischemia often gives rise to stroke), the different symptoms are not coextensive. For example, atherosclerosis can cause problems by aneurysm as well as ischemia. Effective low dose amounts of chloroquine compounds will be useful for prevention, prophylaxis and/or treatment of a combination of these symptoms associated with metabolic syndrome.

The invention is based, in part, on experiments with mouse ATM/Apo-E models and from results in humans with metabolic syndrome. The ApoE-null model mice lacking a single allele of ATM (models for metabolic syndrome) had markedly worse glucose tolerance, increased hypertension, and worse atherosclerosis than normal ApoE-null mice. ApoE-null mice lacking both ATM alleles had even worse symptoms, so much so that many mice failed to survive development or the neonatal period. Treating ApoE-null model mice lacking a single allele of ATM (being fed a high fat diet) with 7 mg/kg of chloroquine per week significantly reduced atherosclerosis, hypertension, glucose intolerance, and central adiposity.

Similarly, preliminary trials in humans with metabolic syndrome showed surprisingly effective low dose amounts of chloroquine compounds (80 mg/day) activated ATM kinase and induced p53 in peripheral blood monocytes of subjects. This low dose chloroquine treatment also improved a number of symptoms in humans with metabolic syndrome including glucose intolerance, atherosclerosis, elevated LDL cholesterol levels, triglyceride levels, and total cholesterol. These experiments also showed that low doses of chloroquine activate ATM and p53 in cultured cells and in isolated patient monocytes.

Aspects of the present invention relate to a number of terms used in accordance with the following definitions.

The term "increasing ATM activity" refers to increasing the level of ATM activity in a mammal with metabolic syndrome, above the level of ATM activity prior to treatment with chloroquine. Typically, the increase in ATM activity will correspond to the prevention of or alleviation of one or more of the symptoms associated with metabolic syndrome.

The term "metabolic syndrome" refers to the following symptoms and features including at least three of the following symptoms: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity).

Chloroquine Compounds

The term "chloroquine compound" as used herein means related aminoquinolines, including chloroquine-like compounds, chloroquine and enantiomers, analogs, derivatives, metabolites, pharmaceutically acceptable salts, and mixtures thereof. Examples of chloroquine compounds include, but are not limited to, chloroquine phosphate, hydroxychloroquine, chloroquine diphosphate, chloroquine sulphate, hydroxychloroquine sulphate, and enantiomers, analogs, derivatives, metabolites, pharmaceutically acceptable salts, and mixtures thereof. The term "chloroquine-like compounds" as used herein means compounds that mimic chloroquine's biological and/or chemical properties.

In a specific embodiment, the invention is practiced with chloroquine. The chemical structure of chloroquine, $N_4$-(7-Chloro-4-quinolinyl)-$N_1$,$N_1$-diethyl-1,4-pentanediamine or 7-chloro-4-(4-diethylamino-1-methylbutylamino) quinoline, is as follows:

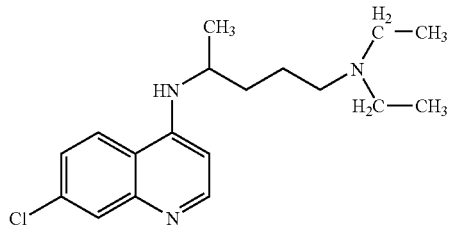 [SMILES: CCN(CC)CCCC(C)Nc1ccnc2cc(Cl)ccc12]

Chloroquine (The Merck Index, p. 2220, 1996) is a synthetically manufactured drug containing a quinoline nucleus. Suitable synthesis techniques for chloroquine are well known in the art. For example see U.S. Pat. No. 2,233,970.

As mentioned above, the chloroquine compounds useful herein include chloroquine analogs and derivatives. A number of chloroquine analogs and derivatives are well known. For example, suitable compounds and methods for synthesizing the same are described in U.S. Pat. Nos. 6,417,177; 6,127,111; 5,639,737; 5,624,938; 5,736,557; 5,596,002; 5,948,791; 5,510,356; 2,653,940; 2,233,970; 5,668,149; 5,639,761; 4,431,807; and 4,421,920.

Examples of suitable chloroquine compounds include chloroquine phosphate; 7-chloro-4-(4-diethylamino-1-butylamino)quinoline (desmethylchloroquine); 7-hydroxy-4-(4-diethylamino-1-butylamino)quinoline; 7-chloro-4-(1-carboxy-4-diethylamino-1-butylamino)quinoline; 7-hydroxy-4-(1-carboxy-4-diethylamino-1-butylamino)quinoline; 7-chloro-4-(1-carboxy-4-diethylamino-1-methylbutylamino)quinoline; 7-hydroxy-4-(1-carboxy-4-diethylamino-1-methylbutylamino)quinoline; 7-chloro-4-(4-ethyl-(2-hydroxyethyl)-amino-1-methylbutylamino)quinoline (hydroxychloroquine); 7-hydroxy-4-(4-ethyl-(2-hydroxy-ethyl)-amino-1-methyl-1-butylamino)quinoline; hydroxychloroquine phosphate; 7-chloro-4-(4-ethyl-(2-hydroxy-ethyl)-amino-1-butylamino)quinoline (desmethylhydroxychloroquine); 7-hydroxy-4-(4-ethyl-(2-hydroxyethyl)-amino-1-butylamino)quinoline; 7-chloro-4-(1-carboxy-4-ethyl-(2-hydroxyethyl)-amino-1-butylamino) quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-hydroxy-4-(1-carboxy-4-ethyl-(-2-hydroxyethyl)-amino-1-methylbutylamino) quinoline; 8-[(4-aminopentyl)amino]-6-methoxydihydrochloride quinoline; 1-acetyl-1,2,3,4-tetrahydroquinoline; 8-[4-aminopentyl)amino]-6-methoxyquinoline dihydrochloride; 1-butyryl-1,2,3,4-tetrahydroquinoline; 7-chloro-2-(o-chlorostyryl)-4-[4-diethylamino-1-methylbutyl]aminoquinoline phosphate; 3-chloro-4-(4-hydroxy-.alpha.,.alpha.'-bis(2-methyl-1-pyrrolidinyl)-2,5-xylidinoquinoline, 4-[(4-diethylamino)-1-methylbutyl)amino]-6-methoxyquinoline; 3,4-dihydro-1(2H)-quinolinecarboxyaldehyde; 1,1'-pentamethylenediquinoleinium diiodide; and 8-quinolinol sulfate, enantiomers thereof, as well as suitable pharmaceutical salts thereof.

Additional suitable chloroquine derivatives include aminoquinoline derivatives and their pharmaceutically acceptable salts such as those described in U.S. Pat. Nos. 5,948,791 and 5,596,002. Suitable examples include (S)—$N_2$-(7-Chloro-quinolin-4-yl)-$N_1,N_1$-dimethyl-propane-1,2-diamine; (R)—$N_2$-(7-chloro-quinolin-4-yl)-$N_1,N_1$-dimethyl-propane-1,2-diamine; $N_1$-(7-chloro-quinolin-4-yl)-2,$N_2,N_2$-trimethyl-propane-1,2-diamine; $N_3$-(7-chloro-quinolin-4-yl)-$N_{-1},N_1$-diethyl-propane-1,3-diamine; (RS)-(7-chloro-quinolin-4-yl)-(1-methyl-piperidin-3-yl)-amine; (RS)-(7-chloro-quinolin-4-yl)-(1-methyl-pyrrolidin-3-yl)-amine; (RS)—$N_2$-(7-Chloro-quinolin-4-yl)-$N_1,N_1$-dimethyl-propane-1,2-diamine; (RS)—$N_2$-(7-chloro-quinolin-4-yl)-$N_1,N_1$-diethyl-propane-1,2-diamine; (S)—$N_2$-(7-chloro-quinolin-4-yl)-$N_1$,$N_1$-diethyl-propane-1,2-diamine; (R)—$N_2$-(7-chloro-quinolin-4-yl)-$N_1,N_1$-diethyl-propane-1,2-diamine; (RS)-7-chloro-quinolin-4-yl)-(1-methyl-2-pyrrolidin-1-yl-ethyl)-amine; $N_2$-(7-chloro-quinolin-4-yl)-$N_1,N_1$-dimethyl-ethane-1,2-diamine; $N_2$-(7-chloro-quinolin-4-yl)-$N_1,N_1$-diethyl-ethane-1,2-diamine; $N_3$-(7-chloro-quinolin-4-yl)-$N_1,N_1$-dimethyl-propane-1,3-diamine; (R)—$N_1$-(7-chloro-quinolin-4-yl)-$N_2,N_2$-dimethyl-propane-1,2-diamine; (S)—$N_1$-(7-chloro-quinoline-4-yl)-$N_2,N_2$-dimethyl-propane-1,2-diamine; (RS)-(7-chloro-quinolin-4-yl)-(1-methyl-pyrrolidin-2-yl-methyl)-amine; $N_1$-(7-Chloro-quinolin-4-yl)-$N_2$-(3-chloro-benzyl)-2-methyl-propane-1,2-diamine; $N_1$-(7-chloro-quinolin-4-yl)-$N_2$-(benzyl)-2-methyl-propane-1,2-diamine; $N_1$-(7-chloro-quinolin-4-yl)-$N_2$-(2-hydroxy-3-methoxy-benzyl)-2-methyl-propane-1,2-diamine; $N_1$-(7-chloro-quinolin-4-yl)-$N_2$-(2-hydroxy-5-methoxy-benzyl)-2-methyl-propane-1,2-diamine; and $N_1$-(7-chloro-quinolin-4-yl)-$N_2$-(4-hydroxy-3-methoxy-benzyl)-2-methyl-propane-1,2-diamine; (1S,2S)—$N_1$-(7-chloro-quinolin-4-yl)-$N_2$-(benzyl)-cyclohexane-1,2-diamine; (1S,2S)—$N_1$-(7-chloro-quinolin-4-yl)-$N_2$-(4-chlorobenzyl)-cyclohexane-1,2-diamine; (1S,2S)—$N_1$-(7-chloro-quinolin-4-yl)-$N_2$-(4-dimethylamino-benzyl)-cyclohexane-1,2-diamine; cis-$N_1$-(7-chloro-quinolin-4-yl)-$N_4$-(4-dimethylamino-benzyl)-cyclohexane-1,4-diamine; cis-$N_1$-(7-chloro-quinolin-4-yl)-$N_4$-(benzyl)-cyclohexane-1,4-diamine; cis-$N_1$-(7-chloro-quinolin-4-yl)-$N_4$-(3-chloro-benzyl)-cyclohexane-1,4-diamine; cis-$N_1$-(7-chloro-quinolin-4-yl)-$N_4$-(2-hydroxy-4-methoxy-benzyl)-cyclohexane-1,4-diamine; cis-$N_1$-(7-chloro-quinolin-4-yl)-$N_4$-(3,5-dimethoxy-benzyl)-cyclohexane-1,4-diamine; cis-$N_1$-(7-chloro-quinolin-4-yl)-$N_4$-(4-methylsulphanyl-benzyl)-cyclohexane-1,4-diamine; cis-$N_1$-(7-chloro-quinolin-4-yl)-$N_4$-(4-diethylamino-benzyl)-cyclohexane-1,4-diamine; cis-$N_1$-(7-chloro-quinolin-4-yl)-$N_4$-(biphenyl-4-yl)methyl-cyclohexane-1,4-diamine; trans-$N_1$-(7-chloro-quinolin-4-yl)-$N_4$-[2-(3,5-dimethoxy-phenyl)-ethyl]-cyclohexane-1,4-diamine; cis-$N_1$-(7-chloro-quinolin-4-yl)-$N_4$-(4-methoxy-benzyl)-cyclohexane-1,4-diamine; trans-$N_1$-(7-chloro-quinolin-4-yl)-$N_4$-(4-dimethylamino-benzyl)-cyclohexane-1,4-diamine; and trans-$N_1$-(7-chloro-quinolin-4-yl)-$N_4$-(2,6-difluoro-benzyl)-cyclohexane-1,4-diamine.

Chloroquine compounds, such as chloroquine, may exhibit the phenomena of tautomerism, conformational isomerism, geometric isomerism, and/or optical isomerism. The invention covers any tautomeric, conformational isomeric, optical isomeric and/or geometric isomeric forms of the chloroquine compounds, as well as mixtures of these various different forms.

Chloroquine and hydroxychloroquine are generally racemic mixtures of (−)- and (+)-enantiomers. The (−)-enantiomers are also known as (R)-enantiomers (physical rotation) and 1-enantiomers (optical rotation). The (+)-enantiomers are also known as (S)-enantiomers (physical rotation) and r-enantiomers (optical rotation). The metabolism of the (+)- and the (−)-enantiomers of chloroquine are described in Augustijins and Verbeke, Clin. Pharmacokin., 1993, 24(3): 259-69; Augustijins, et al., Eur. J. Drug Metabol. Pharmacokin., 1999, 24(1):105-8; DuCharme and Farinotti, Clin. Pharmacokin., 1995, 31(4):257-74; Ducharme, et al., Br. J. Clin. Pharmacol., 1995, 40(2):127-33. Preferably, the (−)-enantiomer of chloroquine is used. The enantiomers of chloroquine and hydroxychloroquine can be prepared by procedures known to the art.

The chloroquine compounds may metabolize to produce active metabolites. The use of active metabolites is also within the scope of the present invention.

Although an understanding of mechanism is not required for practice of the invention, and the present invention is not limited by any particular mechanism, it is believed that one mechanism of action of chloroquine compounds is to enhance the activity of Ataxia-Telangiectasia Mutated (ATM) kinase. The agonistic properties of chloroquine on ATM kinase have been demonstrated (see U.S. Pub. No. 20030077661 entitled "ATM Kinase Compositions and Methods," filed Nov. 27, 2003, which is incorporated by reference herein in its entirety). Hence, chloroquine-like compounds include compounds that are agonists of ATM kinase. Agonists of ATM kinase include compounds that promote the dissociation of ATM into active monomers and/or compounds that promote phosphorylation of a serine corresponding to the residue 1981 of ATM kinase of SEQ ID NO:1. Chloroquine compounds may also be effective via one or other mechanisms that do not involve interaction with ATM.

Use of Chloroquine Compounds

The invention provides methods of prophylaxis or therapeutic treatment of an animal or mammalian subject, including a human. Although an understanding of the mechanism is not required for the practice of the invention, it is believed that chloroquine compounds act in part by protecting normal cells from radiation or free radicals and by inhibiting the cellular damage caused by the radiation or free radicals to normal cells and enhancing the repair process of the normal cells. The methods generally involve the administration of effective amounts of chloroquine compounds for the treatment of one or more the diseases or disorders described in more detail below.

Genetic risk of metabolic syndrome can be associated with either homozygous or heterozygous variations in genes. These variations are present in the germline of the patient. Generally, the most commonly occurring allele in a population is referred to as the wildtype allele, and other less common alleles are referred to as variant alleles. Variant forms associated with metabolic syndrome can be recognized by comparing alleles in populations with and without metabolic syndrome (usually the individuals in the population with metabolic syndrome have the same type for purposes of analysis). Alleles occurring significantly more frequently in the population having metabolic syndrome are associated with metabolic syndrome. A causative relationship can be conferred by transforming the allele into cells or transgenic animals or knocking out an endogenous allele and determining whether the allele causes metabolic syndrome in the transformed cell or animal.

ATM and/or p53 are examples of genes having variations associated with cancer (see, e.g., Garber et al., Cancer Research, 1991, 51: 6094-6097; Olsen et al., J. Nat. Cancer Inst., 2001, 93: 121-127). As noted, these genes are also thought at least in part to affect the prophylactic and therapeutic benefits of chloroquine compounds. Optionally, subjects can be screened for variations in these genes before commencing treatment. Subjects having wildtype forms of ATM or p53, or heterozygous mutations or homozygous mutations leaving residual activity of p53 or ATM are preferred for treatment with chloroquine compounds. Subjects having mutations that effectively eliminate ATM or p53 function are less preferred for treatments with chloroquine compounds as described herein. Individuals missing one allele of ATM or p53 are also preferred for treatment with chloroquine compounds. Any subject with symptoms of metabolic syndrome is envisioned to benefit from treatments with chloroquine compounds as described herein.

Methods for determining presence of genetic variations in individuals are described in "Improvements to Analysis Methods for Individual Genotyping", filed Feb. 24, 2004, U.S. Ser. No. 10/768,788, "Apparatus and Methods for Analyzing and Characterizing Nucleic Acid Sequences", filed Jan. 30, 2003, and U.S. Ser. No. 10/042,819, "Genetic Analysis Systems and Methods", filed Jan. 7, 2002, and EPO 730 663, each of which is incorporated by reference.

Therapeutic and Prophylactic Benefits

Low doses of chloroquine compounds can be used as prophylactic agents. For prophylactic benefit, the chloroquine compound can be administered to a subject at risk of developing metabolic syndrome, but not presently showing symptoms. Individuals at risk for metabolic syndrome include those who exhibit central obesity with increased abdominal girth of about greater than 35 inches in women and about greater than 40 inches in men. Individuals at risk for metabolic syndrome also include those that have a BMI greater than or equal to 30 kg/M$^2$ and may also have abnormal levels of nonfasting glucose, lipids and blood pressure. Genetic risk of metabolic syndrome can be associated with either homozygous or heterozygous variations in genes as described above. A prophylactic benefit is achieved when a disorder is delayed, reduced in severity or prevented from afflicting a subject. A prophylactic benefit can include a result in which the subject is inflicted with a milder form of the disorder than in the absence of treatment or the appearance of fewer or no symptoms of the disorder, or the absence of the disorder in the subject being treated.

Low doses of chloroquine compounds can be used for their therapeutic benefits in treating the numerous or cluster of symptoms associated with metabolic syndrome. A therapeutic benefit includes eradication or amelioration of the underlying disorder being treated. A therapeutic benefit also includes the eradication or amelioration of one or more of the physiological symptoms associated with the underlying disorder such that an improvement is observed in the subject, notwithstanding that the subject may still be afflicted with the underlying disorder. A therapeutic benefit also includes elimination or reduction of consequences of the underlying disorder, such as a reduction in the generation of free radicals and the resulting damage to macromolecules and tissue in atherosclerosis, stroke, ischemia and oxidative stress. A therapeutic benefit can also result when administration of a chloroquine compound inhibits or prevents further deterioration in the patient's condition of an existing disorder.

Dosage and Dosage Regimen

Pharmaceutical compositions suitable for use in the present invention include compositions wherein the chloroquine compound and other optional active ingredients are present in an effective amount for treating or preventing metabolic syndrome.

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

In some methods, the effective amount includes the dose ranges, modes of administration, formulations, and so forth, that have been recommended or approved by any of the various regulatory or advisory organizations in the medical or pharmaceutical arts (e.g., FDA, AMA) or by the manufacturer or supplier. Effective amounts of chloroquine can be found, for example, in the Physicians Desk Reference. Chloroquine can be administered orally, in the form of chloroquine phosphate, or by injection or i.v., in the form chloroquine hydrochloride. See generally, Physician's Desk Reference, Medical Economics Company, Inc., Montvale, N.J. (54th Ed. 2000), at pp. 2733-2735.

In some methods, the daily low dosage range of chloroquine, can vary between about 3.5 mg/kg to about 7.0 mg/kg body weight. In other methods, the dose range may be even lower, from about 0.1 mg/kg/day through about 3.0 mg/kg/day. Some daily doses of chloroquine diphosphate range from about 3.5 mg/kg through about 7.0 mg/kg.

The dosage can vary depending on the subject being treated. For example, a preferred dosage in mice is about 3.5 mg/kg once or twice a day. The equivalent dosages in monkeys and humans are shown in the Table 1.

TABLE 1

| Mouse (20 g) | Monkey (3 kg) | Man (60 kg) | Man (60 kg) CHQ Equivalent |
|---|---|---|---|
| 3.5 mg/kg | 0.875 mg/kg | 0.292 mg/kg | 17.5 mg CHQ |
| 7.0 mg/kg | 1.75 mg/kg | 0.583 mg/kg | 35.0 mg CHQ |

Preferred dosages ranges in human include from about 0.1 to about 3 mg/kg/day, more preferably from about 0.6 mg/kg/day to about 3 mg/kg/day. Another preferred dosage range in humans includes from about 0.8-1.2 mg/kg per day. Another preferred dosage range in humans includes from about 0.1 mg/kg to about 9 mg/kg once a week. A particularly preferred dosage in humans includes about 80 mg per day. Another dosage in humans includes about 40 mg per day. The dosage can be administered daily, weekly, monthly or bimonthly (every two months). For patients subject to a chronic risk (e.g., through genetic variation), the dosage is preferably administered weekly, monthly or bimonthly for an indefinite period. The dosage range can be lower e.g., about 0.1 to about 0.2 mg/kg per day or per week of chloroquine if a purified (−) enantiomer is used. If hydroxychloroquine is used the dosage range is usually higher than if chloroquine is used.

Pharmaceutically active compounds suitable for use in combination with chloroquine compounds of the present invention may include an effective amount of compounds such as antihypertensive agents including □-receptor blocker (beta-blockers), angiotensin converting enzyme inhibitors (ACE inhibitors), angiotensin receptor blockers (ARBs), and calcium channel blockers, inhibitors of cholesterol synthesis and absorption, antithrombotic agents, and antihyperglycemic diabetes treatments including insulin or an insulin analog, actos (pioglitazone), avandia (rosiglitazone), sulfonylureas such as acetohexamide, amaryl (glimepiride), chlorpropamide, glipizide, glyburide, avandia (rosiglitazone); or tolbutamide, a biguanide-type medication such as glucophage, glucotrol, glucagon, or glucovance (a combination of glyburide and metformin), phentolamine, or tolazemide. Mixtures of any of the above agents including any pharmaceutically acceptable salt form of these agents, may be used in combination with the chloroquine compounds of the present invention. Each of these agents may be produced by methods known in the art. These agents may also be administered at the pharmaceutically or therapeutically effective dosages or amounts known in the art for these compounds, such as those described in the Physician's Desk Reference 2001, 55 Edition, Copyright 2001, published by Medical Economics Company, Inc., the relevant portions describing each of these products being incorporated herein by reference. U.S. Pat. Nos. 6,610,272 and 6,734,197 describe a number of diabetic treatments with typical dosing and effective amounts, and each of these patents is hereby incorporated by reference in its entirety.

In some methods, the effective amount of chloroquine or other pharmaceutically active compound is administered at regular intervals, such as every other week, once a week, more than once a week, or once a day. The dose of chloroquine or other pharmaceutically active compound can be administered once or more than once a day. In some methods, the effective amount of a chloroquine compound is an amount that produces the intended beneficial effects but does not produce the side-effects associated with chloroquine compounds, like retinoblastoma.

Kits

The invention provides a kit comprising a chloroquine compound packaged in association with instructions teaching a method of using the compound according to one or more of the above-described methods. The kit can contain the chloroquine compound packaged in unit dosage form. The kit may also contain additional pharmaceutically active agents or compounds including unit dosage forms of compounds such as antihypertensive agents including □-receptor blockers (beta-blockers), angiotensin converting enzyme inhibitors (ACE inhibitors), angiotensin receptor blockers (ARBs), and calcium channel blockers, inhibitors of cholesterol synthesis and absorption, antithrombotic agents, and diabetes treatments. Typical unit dose forms of certain cholesterol lowering drugs and ACE inhibitors are well known and described in U.S. Pat. No. 5,190,970, which is hereby incorporated by reference in its entirety. Typical unit dose forms of antithrombotic agents and calcium channel blockers are well known and are described by Coull et al., Stroke, 2002, 33:1934-1942. Typical unit dose forms of beta-blockers are well known in the art and are described in U.S. Pat. Nos. 6,756,408 and 6,933,279. Typical diabetes treatments and dosages are well known in the art and are described in U.S. Pat. No. 6,610,272. Embodiments of various methods and combination involving chloroquine treatment and chloroquine combination treatments are described in more detail in the following sections.

Routes of Administration and Formulation

The compounds useful in the present invention, or pharmaceutically acceptable salts thereof, can be delivered to the subject using a wide variety of routes or modes of administration. Suitable routes of administration include, but are not limited to, inhalation, transdermal, oral, rectal, transmucosal, intestinal and parenteral administration, including intramuscular, subcutaneous and intravenous injections. A preferred mode of administration includes in oral dosage form. An embodiment of the present invention includes a dosage formulation containing about 1 mg to about 140 mg of a chloroquine compound along with a pharmaceutically acceptable salt. A preferred embodiment includes a dosage formulation containing about 80 mg of a chloroquine compound along with a pharmaceutically acceptable salt. Any dosage formulation containing less than about 140 mg, including about 40 mg of a chloroquine compound will useful for long term treatment of individuals with metabolic syndrome. Long term treatment refers to an extended period of time, typically longer than two weeks, and includes any length of time whereby the individual/subject (mammal) exhibits improvement in metabolic syndrome symptoms. This dosage formulation will be beneficial for prophylactic treatment of individuals who will be taking low dosages of chloroquine for extended periods of time to prevent metabolic syndrome.

The chloroquine compounds can be administered topically or systemically. Systemic administration is preferred. In some methods, topical administration also has a systemic effect.

The term "pharmaceutically acceptable salt" means those salts which retain the biological effectiveness and properties of the compounds used in the present invention, and which are not biologically or otherwise undesirable. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

Agents used in accordance with the methods of the invention can be conveniently administered in a pharmaceutical composition containing the active compound in combination with a suitable carrier. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams and Wilkins: Philadelphia, Pa., 2000.

A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject.

Examples of materials which can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; lycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Agents of use in the invention can be administered parenterally (for example, by intravenous, intraperitoneal, subcutaneous or intramuscular injection), topically (including buccal and sublingual), orally, intranasally, intravaginally, or rectally, with oral administration being particularly preferred.

For oral therapeutic administration, the composition can be combined with one or more carriers and used in the form of ingestible tablets, buccal tablets, troches, capsules, elixirs, suspensions, syrups, wafers, chewing gums, foods and the like. Also, for oral consumption the active ingredient can be dissolved or suspended in water or other edible oral solutions. Such compositions and preparations should contain at least 0.1% of active compound. The percentage of the compositions and preparations can, of course, be varied and can conveniently be between about 0.1 to about 100% of the weight of a given unit dosage form. The amount of active agent in such therapeutically useful compositions is such that an effective dosage level is obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like.

For administration orally, the compounds can be formulated as a sustained release preparation. Numerous techniques for formulating sustained release preparations are described in the following references—U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491. These references are hereby incorporated herein by reference in their entireties. In a preferred embodiment, the sustained release formulation utilized has an enteric coating.

For administration by inhalation, the active compound(s) can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

A syrup or elixir can contain the active agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active components can be incorporated into sustained-release preparations and devices including, but not limited to, those relying on osmotic pressures to obtain a desired release profile. Once daily formulations for each of the active components are specifically included.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation or transcutaneous delivery (for example subcutaneously or intramuscularly), intramuscular injection or a transdermal patch. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The selected dosage level depends on a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors wellknown in the medical arts.

If necessary, the compounds as used herein can be administered in combination with other therapeutic agents or regimes as discussed. The choice of therapeutic agents that can be co-administered with the compounds of the invention depends, in part, on the condition being treated. For example the chloroquine compounds of the present invention can be administered as the sole pharmaceutical agent or in combination with one or more other pharmaceutical agents or compounds where the combination provides desired effects. Certain methods of the present invention also include administering an effective amount of one or more additional pharmaceutically active compound such as antihypertensive agents including beta-blockers, angiotensin converting enzyme inhibitors (ACE inhibitors), and calcium channel blockers, inhibitors of cholesterol synthesis, antithrombotic agents, and diabetes drugs such as insulin or actos (pioglitazone), sulfonylureas such a amaryl (glimepiride), glipizide; avandia (rosiglitazone); a biguanide-type medication such as glucophage; glucotrol; and glucovance (a combination of glyburide and metformin).

"A combination amount sufficient," "an effective combination amount" "therapeutically effective combination amount" or "an effective amount of the combination of" all refer to combined amounts of a chloroquine compound and any additional pharmaceutically active ingredients (e.g., antihypertensive, cholesterol lowering, and/or antidiabetic agents) that is effective to ameliorate symptoms associated with metabolic syndrome. As used herein, the term "combination" of a chloroquine compound and at least a second pharmaceutically active ingredient means at least two, but any desired combination of compounds can be delivered in a simultaneous manner (meaning administered or delivered within a 24 hour period), in combination therapy wherein the chloroquine compound is administered first, followed by the second or more pharmaceutically active ingredient(s), as well as wherein the second pharmaceutically active ingredient is delivered first, followed by a chloroquine compound. The desired result can be either a subjective relief of a symptom(s) or an objectively identifiable improvement in the recipient of the dosage.

The terms "synergistic effective amount" may refer to a combined amount of a chloroquine compound and at least one of a antihypertensive, antithrombic, cholesterol lowering, and/or antidiabetic agent that is effective to cause a synergistic effect in the mammal in need of treatment. Synergy is a biological phenomenon in which the effectiveness of two active components in a mixture is more than additive, i.e., the effectiveness is greater than the equivalent concentration of either component alone. For example, the effectiveness of the combination therapy of a chloroquine compound and an antidiabetic agent is expected to be synergistic. Thus, synergism is a result, or function, that is more than the sum of the results, or functions of individual elements.

Administration of Chloroquine in Combination with Additional Treatments

Chloroquine compounds may be used in conjunction with virtually any inhibitors of cholesterol synthesis or absorption, including any of the family of substances known as Hmg-CoA reductase inhibitors. Hmg-CoA reductase inhibitors are taught for example in U.S. Pat. Nos. 4,346,227 4,857,522, 5,190,970, and 5,461,039, each of which is hereby incorporated by reference in its entirety. Hmg-CoA reductase inhibitors are exemplified by, but not limited to atorvastatin and pravastatin. Particular Hmg-CoA reductase inhibitors preferred for use in conjunction with the present chloroquine formulation include: simvastatin, lovastatin, pravastatin, compactin, fluvastatin, dalvastatin, HR-780, GR-95030, CI-981, BMY 22089, and BMY 22566. U.S. Pat. No. 5,316,765 describes a number of these Hmg-CoA reductase inhibitors and is hereby incorporated by reference in its entirety. The preparation of XU-62-320 (fluvastatin) is described in WIPO Patent WO84/02131. BMY 22089 is described in GB Patent No. 2,202,846. Pravastatin sodium is described in U.S. Pat. No. 4,346,227 while simvastatin is described in U.S. Pat. No. 4,444,784, each of which is hereby incorporated by reference in its entirety.

Also included for use in conjunction with chloroquine compounds of the present invention are the bio-active metabolites of Hmg-CoA reductase inhibitors, such as pravastatin sodium (the bio-active metabolite of mevastatin).

As used in methods or compositions of the present invention, any one or several of the Hmg-CoA reductase inhibitor compounds may be mixed with L-arginine or a substrate precursor to endogenous nitric oxide, as described in U.S. Pat. Nos. 6,425,881 and 6,239,172, and 5,968,983, each of which is hereby incorporated by reference in its entirety, to provide a therapeutically effective mixture for use in conjunction with chloroquine compounds of the present invention.

An embodiment of the present invention includes administering a chloroquine compound along with second pharmaceutically active ingredient that includes various diabetes treatments such as insulin or insulin analogs, or other diabetes drugs such as: actos (pioglitazone), sulfonylureas such a amaryl (glimepiride), glipizide; avandia (rosiglitazone); a biguanide-type medication such as glucophage; glucotrol; and glucovance (a combination of glyburide and metformin). The term diabetic aid includes natural, synthetic, semi-synthetic and recombinant medicaments such as activin, glucagon, insulin, somatostatin, proinsulin, amylin, and the like. Many of these diabetic treatments are described in U.S. Pat. No. 6,610,272, which is herein incorporated by reference in its entirety.

The term "insulin" encompasses natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

In accordance with the present invention, administering low dose chloroquine in combination with insulin will lower the dose of insulin required to manage the diabetic patient, while also alleviating the symptoms of metabolic syndrome.

Additional pharmaceutically active ingredients or compounds utilized in combination with the chloroquine compositions of the present invention may include any of the following types of compounds including anti-inflammatory agents, antioxidants, antiarrhythmics, cytokines, antihypertensives, analgesics, vasodilators, and peptides.

Combination Treatments in View of Oxidative Stress

An embodiment of the present invention includes administering an effective amount of a chloroquine compound along with one or more measures to combat oxidative stress. Such measures including changes in diet, for example, increased intake of fruit and vegetables, and supplementation of the diet with phytochemicals or antioxidants, such as vitamin B12. Such measures also include increased exercise, and decreased occupational stress. Such measures also include administration of drugs with antioxidant activity such as methylprednisolone, 21-aminosteroids, 2-methylaminochromans, pyrrolopyrimidines and thiazolidinones. Although an understanding of mechanism is not required for practice of the invention, it is believed that administration of a chloroquine compound serves to stimulate the cellular response to DNA damage and promote the repair of the cells exposed to radicals generated by oxidative stress.

In some methods, a chloroquine compound is administered to a subject exhibiting or at risk of ischemia in combination with a second agent or a second pharmaceutically active ingredient effective in prophylaxis or treatment of damage resulting from ischemia and/or reperfusion. Such agents include antibodies to adhesion molecules such as L-selectin, or CD18, tissue plasminogen activator (see EP-B 0 093 619), activase, alteplase, duteplase, silteplase, streptokinase, anistreplase, urokinase, heparin, warfarin and coumarin. Additional thrombolytic agents include saruplase and vampire bat plasminogen activator.

Subjects at risk of ischemia include those having previously had heart disease, those having elevated biochemical markers of the disease (e.g., C-reactive protein), those identified as having blockage of blood vessels by angioplasty or MRI imaging, those with deficiencies in or resistance to activated protein C, and those undergoing a surgical procedure requiring temporary obstruction of blood vessels. The presence or absence and the amount of myocardial damage resulting from prolonged ischemia can be assessed by a number of different means, including pathologic examination, measurement of myocardial proteins in the blood, ECG recordings (ST-T segment wave changes, Q waves), imaging modalities such as myocardial perfusion imaging, echocardiography, contrast ventriculography or positron emission tomography (see, e.g., Hanninen et al. Int. J. Bioelectromagnetism, 2000, No. 1 Vol. 2; and Alpert, J. Am. College. Cardiol., 2000, 36:959-69). Myocardial necrosis results in and can be recognized by the appearance in the blood of different proteins released into the circulation due to the damaged myocytes: myoglobin, cardiac troponins T and I, creatine kinase, and lactate dehydrogenase. The response of the subject to treatment with a chloroquine compound in combination with a second agent or a second pharmaceutically active ingredient effective in prophylaxis or treatment of damage resulting from ischemia and/or reperfusion can be monitored by any of these tests. Preferably, the amount of pathological damage or level of a marker associated with the same shows a reduced increase, does not increase, or even is reduced following administration of a chloroquine compound relative to a placebo.

Combination Treatments Related to Stroke

Administration of chloroquine can be accompanied by administration of additional agents or pharmaceutically active ingredients to treat stroke. These include the same agents discussed for treating ischemia and oxidative stress as described above. Multiple symptoms may be present in a stroke patient, and it is believed that a combination treatment with chloroquine and another active agent effective in prophylaxis or treatment of damage resulting from ischemia and/or reperfusion would provide added benefits to the patient. Examples of these agents include antithrombotic agents such as unfractionated heparin, low molecular weight (LMW) heparin, heparinoids, aspirin, ticlopidine, clopidogrel, dipyridamole, hirudin, and glycoprotein IIb/IIIa antagonists, as described by Coull et al. Stroke, 2002, 33:1934-1942, which is hereby incorporated by reference in its entirety.

Subjects at risk of stroke can be determined by presence of one, and usually at least two of the following risk factors: high blood pressure, heart disease, high cholesterol levels, sleep apnea, previous occurrence of stroke, smoking, excessive alcohol consumption and excessive weight. Alternatively, transcranial doppler (TCD) testing uses sound waves to measure the speed with which blood flows through the large blood vessels within the head. The test can detect constriction (narrowing) of blood vessels as well as blood flow abnormalities related to cerebrovascular disease. Damage to tissue from stroke can be monitored by MRI and/or by cognitive testing. Monitoring of tissue damage, if any, can be performed following administration of the combination chloroquine treatments described herein.

Combination Treatments Related to Atherosclerosis

Administration of a chloroquine compound for treating metabolic syndrome can also be combined with any desired agents conventionally used in prophylaxis or treatment of atherosclerosis. These include antithrombotic agents such as unfractionated heparin, low molecular weight (LMW) heparin, heparinoids, aspirin, ticlopidine, clopidogrel, dipyridamole, hirudin, and glycoprotein IIb/IIIa antagonists. Also included are lipid lowering agents such as statins, ezetimibe, bile acid sequestrants, fibrates, HMG-CoA reductase inhibitors, nicotinic acid derivatives, and blood pressure lowering agents.

Additional pharmacologically active agents may be delivered along with the primary active agents, e.g., the chloroquine compounds of the invention. In one embodiment, such agents include, but are not limited to agents that reduce the risk of atherosclerotic events and/or complications thereof. Such agents include, but are not limited to beta blockers, beta blockers combined with thiazide diuretic combinations, statins, aspirin, ACE inhibitors, ACE receptor blockers/inhibitors (ARBs), and the like, as described in U.S. Pat. No. 6,933,279.

Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like. Suitable beta blocker thiazide diuretic combinations include, but are not limited to Lopressor HCT, ZIAC, Tenoretic, Corzide, Timolide, Inderal LA 40/25, Inderide, Normozide, and the like. The use of beta blockers is also described in U.S. Pat. No. 6,756,408, which is hereby incorporated by reference in its entirety.

Suitable ACE inhibitors include, but are not limited to captopril (e.g. Capoten™ by Bristol-Myers Squibb), benazepril (e.g., Lotensin #2122; by Novartis), enalapril (e.g., Vasotec™ by Merck), fosinopril (e.g., Monopril™ by Bristol-Myers Squibb), lisinopril (e.g. Prinivil™ by Merck or Zestril™ by Astra-Zeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

Optionally, the methods are practiced on subjects that are free of diseases of the immune system, infectious diseases, neurological diseases, and multidrug resistance (i.e. resistance to multiple drugs for treatment of the same conditions, such as two anti-cancer drugs, or two antibiotics) before commencing administration of the chloroquine compound. Optionally, the methods are practiced on subjects free of psoriasis, malaria, protozoal infections, Alzheimer's disease, Parkinson's disease, lupus erythematosus, rheumatism, hypercalcemia, multiple sclerosis and migraine before administering the chloroquine compound.

III. EXAMPLES

The following examples are included to demonstrate preferred embodiments of the invention. It should be appreciated

Example 1

ATM Mouse Models

Methods

The ATM mutation was moved into the apoE null mouse model to create an ATM$^{-/-}$ apoE$^{-/-}$ mouse model for evaluating the role of ATM in vascular disease. The apoE null mouse model was described by Plump and Breslow in Annu. Rev. Nutr., 1995, 15:495-518, which is hereby incorporated by reference in its entirety. ATM$^{-/-}$ mice and conditions for breeding are described by Spring, K. et al. in Nat. Genet., 2002, 32(1):185-90, which is hereby incorporated by reference in its entirety. The ATM-deficient mice carry a neo gene to interrupt exon 57 and replace exon 58 of ATM (GenBank Accession No. U55702, SEQ ID NO:2), deleting a region of the p13K domain that is also deleted in a number of individuals with ataxia telangiectasia. Originally in a mixed genetic background (C57BL/6 and 129Sv), these mice have been backcrossed with BL/6 mice for more than 6 generations. These backcrossed ATM$^{+/-}$ mice were intercrossed to obtain ATM deficient littermates or bred with apoE-null or LDLR-null mice in the C57BL/6 background. Multiple different breeding pairs were utilized to generate ATM$^{+/+}$apoE$^{-/-}$, ATM$^{+/-}$apoE$^{-/-}$, and ATM$^{-/-}$apoE$^{-/-}$ littermates that were used for experiments. Animals were genotyped at the ATM locus using a forward wild-type primer (5'-AAGATGCTGT-CATGCAGCAGGTCTTCCAGA-3') (SEQ ID NO:3), a reverse neo-specific primer (5'-AATTCTCTA-GAGCTCGCTGATCAGCCTCGA-3') (SEQ ID NO:4), and a reverse wild-type primer (5'-TTGTCCAACCT-GAGAGTGGCAATCCATAGC-3') (SEQ ID NO:5). Mice housed in a specific pathogen-free barrier facility were weaned at the age of three weeks to standard mouse chow providing 6% calories as fat.

ATM Deficiency Phenocopies the Metabolic Syndrome

All experiments were performed using littermates. ATM haploinsufficiency had no effect on breeding or viability in apoE null mice, but ATM$^{-/-}$apoE$^{-/-}$ animals were born at decreased frequency (about 9% versus the expected 25% in ATM$^{+/-}$ apoE$^{-/-}$×ATM$^{+/-}$ apoE$^{-/-}$ matings). This effect appeared to be due to fetal loss in utero; when ATM$^{-/-}$apoE$^{-/-}$ mice were born, they were viable and resembled ATM heterozygotes.

For most experiments, sex-matched animals at the age of 6-8 weeks were started on a high fat Western-type diet consisting of a semipurified diet (TD88137, from Harlan, Madison, Wis.) containing 0.15% cholesterol and providing 42% calories as fat. This diet is typically used in murine models of atherosclerosis. After 8 weeks on this diet, there was no difference in total body weight between ATM$^{+/+}$, ATM$^{+/-}$, and ATM$^{-/-}$ mice in the apoE$^{-/-}$ model (determined for 12 ATM$^{+/+}$, 17 ATM$^{+/-}$, and 4 ATM$^{-/-}$ mice). However, ATM deficient mice had increased adiposity (body fat of about 33% or 31%, compared to about 23% for ATM$^{+/+}$ mice) due in part to increased intra-abdominal fat. Adiposity was determined by DEXA with P<0.05 by ANOVA; and was also observed through en bloc dissections of visceral fat (e.g. whole mounts of visceral fat pads removed en bloc from age-matched ATM$^{+/+}$, ATM$^{+/-}$, and ATM$^{-/-}$ mice). There was no effect of genotype on metabolic rate measured by indirect calorimetry or food intake. Consistent with the adiposity data, adiponectin levels were decreased in ATM deficient mice. Serum adiponectin levels in apoE$^{-/-}$ mice with different ATM genotypes ($\geq 5$ in each group) were determined before and after Western diet feeding for 3 and 8 weeks. Individually tested, ATM$^{+/-}$ levels were at borderline significance different from ATM$^{+/+}$ at baseline and 3 weeks, and significantly different from ATM$^{+/+}$ at 8 weeks.

Blood pressure was elevated in ATM-deficient apoE$^{-/-}$ mice on the Western diet. Systolic blood pressure (SBP) and diastolic blood pressure (DBP) were measured after 8 weeks of Western diet feeding in ATM$^{+/+}$, ATM$^{+/-}$, and ATM$^{-/-}$ mice. With Western diet feeding in the ATM deficient apoE null mice, both systolic and diastolic blood pressures (determined by tail cuff) were elevated in ATM-deficient mice. A plethysmography device (such as those supplied by Kent Scientific, Litchfield, Conn.) was used for tail cuff blood pressure determinations in acclimated, warmed mice performed by a technician blinded to treatment status, according to the manufacturer's instructions. Results were reported as the mean of 5-8 measurements on each day of 3 consecutive days. If appropriate, blood pressure determinations are confirmed invasively under anesthesia or with implantable telemetry sensors.

For the chloroquine experiments, mice were treated with either chloroquine diphosphate (Sigma, St. Louis, Mo.) in 0.9% saline or saline alone administered at 7 mg/kg body weight per week after a loading dose of 7 mg/kg. Two month old male db/db (Lepr$^{db}$; LEPR-deficient mice having excess adiposity) mice and ob/ob (Lep$^{ob}$, genetically obese) mice were purchased from Harlan (Indianapolis, Ind.) and the Jackson Laboratory, respectively.

Western diet-fed ATM$^{+/-}$apoE$^{-/-}$ mice were glucose intolerant and insulin resistant compared to ATM$^{+/+}$apoE$^{-/-}$ littermates. The intraperitoneal glucose tolerance testing was conducted on 9 ATM$^{+/+}$ and 10 ATM$^{+/-}$ littermate mice after 8 weeks on Western diet. Effects on adiposity, blood pressure and glucose metabolism were seen in both genders and replicated in several littermate cohorts. Thus, the ATM$^{+/-}$ genotype, which may be present in 0.5 to 2% of human populations, models at least three components of the metabolic syndrome in apoE null mice: increased adiposity, elevated blood pressure, and glucose intolerance.

Fasting cholesterol, triglycerides, and free fatty acids were not significantly affected by genotype at baseline (on chow diet) or after 3 or 8 weeks of Western diet. The lipid chemistries and atherosclerosis in apoE$^{-/-}$ mice with different ATM genotypes were determined after Western diet feeding for 8 weeks. Fasting glucose and insulin levels increased with Western diet feeding and glucose was highest in ATM$^{-/-}$ animals. Serum adiponectin levels were determined in apoE$^{-/-}$ mice with different ATM genotypes ($\geq 5$ in each group) before and after Western diet feeding for 3 and 8 weeks. Individually tested, ATM$^{+/-}$ levels were at borderline significance different from ATM$^{+/+}$ at baseline and 3 weeks, and significantly different from ATM$^{+/+}$ at 8 weeks. Lipoproteins were not affected by genotype. Atherosclerosis after 8 weeks on the Western diet was increased in ATM-deficient mice inversely based on gene dosage. Atherosclerosis data was assayed by the en face technique for the mice. The P value indicates the overall results of the Kruskal-Wallis test. In post tests, ATM$^{+/+}$ mice showed significant differences (P<0.05) as compared to each of the other two genotypes. The same effects were seen in both males and females. Atherosclerosis was measured in apoE$^{-/-}$ mice with different ATM genotypes according to the gender after Western diet feeding for 8 weeks. The P values indicate the overall results of the Kruskal-Wallis test. These values are different from a similar test group because this data set presents the analysis of 6 groups as compared to 3 in the prior group. In post tests, male ATM$^{+/+}$ mice showed less lesion area vs. male ATM$^{-/-}$ mice (P<0.05) at the arch, and vs. ATM$^{+/-}$ and ATM$^{-/-}$ mice (p<0.05) in the thoracic and abdominal aorta. Female ATM$^{+/+}$ mice showed less atherosclerosis as compared to ATM$^{-/-}$ mice (p<0.05) in the abdominal aorta. In independent assessments, ATM$^{+/+}$ mice of both genders showed significant differences (P<0.05) as compared to each of the other two genotypes.

Insulin Resistance in ATM Deficiency

In hyperinsulinemic-euglycemic clamp experiments conducted in littermates eating the high fat Western diet, endogenous glucose production was suppressed by insulin in ATM$^{+/+}$apoE$^{-/-}$ but not ATM$^{+/-}$apoE$^{-/-}$ mice. Hyperinsulinemic euglycemic clamp data was determined in ATM$^{+/+}$ and ATM$^{+/-}$ mice for 4 animals of each genotype.

Consistent with the presence of hepatic insulin resistance, IRS-2-associated PI 3-kinase activity was decreased in the livers of insulin-stimulated high fat-fed ATM+/− mice. The IRS-2 (liver) and IRS-1 (skeletal muscle)-associated PI 3-kinase activity was determined in post-clamp tissues of ATM$^{+/+}$ and ATM$^{+/-}$ mice by ELISA after immunoprecipitation of the IRS-containing complex. Phosphorylated Akt, a target of PI 3-kinase, was also decreased in the livers of the same insulin-stimulated mice (determined by Western blot analysis of phospho-Akt (Ser473) in post-clamp liver of ATM$^{+/+}$ and ATM$^{+/-}$ mice), consistent with the presence of hepatic insulin resistance in high fat-fed ATM+/− mice. Insulin-induced phosphorylation of Akt at both Ser 473 and Thr 308 was decreased in ATM-deficient livers of apoE null mice as well as low density lipoprotein receptor null mice, another model shown to have increased insulin resistance with ATM deficiency. The baseline and insulin-stimulated Akt-phosphorylation in livers of apoE null mice and LDLR null mice of each ATM genotype were determined by Western blot analysis. The Western blot analysis of phospho-Akt (Ser473) and phospho-Akt (Thr308) of one saline- and one or two insulin-treated animals for each genotype showed decreased liver Akt-phosphorylation with ATM deficiency in these two different mouse backgrounds.

Impaired insulin signaling was present in other ATM-deficient cell types. Decreased IRS expression causes insulin resistance. mRNA as well as protein levels for IRS-2 were decreased in macrophages elicited from ATM-deficient mice. Quantitative RT-PCR determination of IRS-2 expression was performed in thioglycollate-elicited macrophages from ATM$^{+/+}$, ATM$^{+/-}$, and ATM$^{-/-}$ mice. Data were determined relative to GAPDH expression (mean±s.e.m.). *P<0.001. IRS-2 mRNA expression was also analyzed in liver but did not detect consistent genotype effects.

Activated Akt and the related kinases p38 and ERK were decreased in the aortas of young chow-fed ATM-deficient mice. Western blots showed aortic content of phospho-p38, phospho-Akt, and phospho-ERK compared with total p38 protein. The same results were detected in several samples. Young, chow-fed mice without atherosclerotic lesions were used for the aortic analyses. Insulin signaling can be disrupted by a serine phosphorylation at residue 307 of IRS-1. Aortic tissue from ATM$^{-/-}$ mice had the highest level of IRS-1 Ser 307 phosphorylation, ATM$^{+/-}$ aortas were intermediate, and ATM$^{+/+}$ vessels lowest. IRS-1 phosphorylation was detected at position Ser307, normalized to total IRS-1 protein, as acquired by densitometric image analysis of the Western blots. The same results were observed in 2 or more independent experiments for each assay.

Jun N-terminal kinase (JNK) phosphorylates IRS-1 at serine 307 to cause insulin resistance. JNK was activated in aortas in proportion to the degree of ATM deficiency. Phospho-JNK, normalized to total JNK, was detected in whole aorta as determined by quantitative Western blot analysis.

When cultured aortic smooth muscle cells were treated with a morpholino antisense oligonucleotide to ATM, JNK activity was increased, providing direct evidence that interfering with ATM expression induces JNK activity, a mediator of insulin resistance. Analysis of phospho-JNK in vascular smooth muscle cells cultured from ATM$^{+/+}$apoE$^{-/-}$ mice. Primary aortic smooth muscle cells were transfected with an anti-ATM oligonucleotide, or a control oligonucleotide or the vehicle ethoxylated polyethylenimine solution only. Cells were assayed by ELISA for phospho-JNK and total JNK as measured in U/ml/well of a 96-well plate. The results showed phospho-JNK normalized to total JNK of wells with the same treatment condition. These results are consistent with the presence of systemic insulin resistance, JNK activity (as well as phosphorylation of c-Jun, the major JNK substrate) was also increased in adipose tissue, skeletal muscle, and liver of ATM-deficient mice. Increased expression of phospho-JNK was detected in tissues involved in systemic insulin action in all three ATM genotypes in apoE$^{-/-}$ mice, as determined by analysis of Western blots for fat, skeletal muscle and liver. Comparisons were made between ATM-deficient and ATM wild-type animals.

Analytical Procedures

Cholesterol, triglycerides and nonesterified fatty acids (NEFA) were assayed as described following a 4 h fast. For glucose tolerance and insulin tolerance tests, mice were fasted and injected with 10% D-glucose (1 g/kg) or human regular insulin (0.75 units/kg body weight, Eli Lilly and Co., Indianapolis, Ind.) in procedures separated by at least one week. Tail vein blood (5-10 □l) was assayed for glucose at 0, 30, 60, and 120 minutes. Blood glucose was assayed using a glucose meter (Hemocue, Mission Viejo, Calif. or Becton Dickinson, San Jose, Calif.). The area under the glucose and insulin curves (AUC) during the OGTT and ITT were calculated using the formula: 0.25 (fasting value)+0.5 (½ h value)+0.75 (1 h value)+0.5 (2 h value). Body composition was performed on anesthetized, living mice by dual energy X-ray absorptiometry (PIXImus, GE Corporation).

Atherosclerosis Quantification

Atherosclerosis was measured using the en face or aortic origin technique. For the former, pinned aortas were imaged with a digital camera and analyzed by using an image-processing program. The percentage of involvement of the intimal surface area is reported for the arch (encompassing the surface from the aortic valve to the left subclavian artery), the thoracic aorta (extending to the final intercostal artery), and the abdominal aorta (to the ileal bifurcation). For the aortic origin technique, mean lesion size for each animal was quantified by the degree of lipid staining of cross-sections of aortic tissue as described. Anesthetized mice were exsanguinated, the heart and aortic arch were perfused, then tissues were removed en bloc and frozen immediately in tissue freeze medium. For each sample, 64 sections were made on a cryostat beginning just caudal to the aortic sinus and extending into the proximal aorta at 10 μm intervals. Slides were fixed with 60% isopropanol and stained with Oil Red O. For each heart, lesions in eight sections at 80 µm intervals were quantified using image analysis software calibrated using a hemocytometer grid.

ATM heterozygotes (+/−) in the ApoE null model also had glucose intolerance and were insulin resistant as measured in insulin tolerance tests. The glucose tolerance and insulin tolerance tests were performed on mice that were fasted for 12 hours and then injected with 10% D-glucose (1 g/kg) or human regular insulin (0.75 units/kg body weight, Eli Lilly and Co., Indianapolis, Ind.) in procedures separated by at least one week. Tail vein blood (5-10 µl) was assayed for glucose at 0, 30, 60, and 120 minutes. Blood glucose was assayed using a glucose meter (Hemocue, Mission Viejo, Calif.). The area under the glucose and insulin curves (AUC) during the OGTT and ITT were calculated using the formula: 0.25 (fasting value)+0.5 (½ h value)+0.75 (1 h value)+0.5 (2 h value), as described by Haffner et al., N. Engl. J. Med., 1986, 315:220-224.

The phenotype was unaffected by gender and was observed in multiple cohorts of littermates. Thus, the ATM$^{+/-}$ genotype, which may be present in up to 2% of the general population, models at least three components of metabolic syndrome in ApoE null mice: increased visceral adiposity, elevated blood pressure, and glucose intolerance.

Fasting cholesterol, triglycerides, and free fatty acids were not affected by genotype at baseline (on chow diet) or after 3 or 8 weeks of Western diet. Fasting glucose and insulin levels increased with Western diet feeding and glucose was highest in ATM$^{-/-}$ animals, as shown in Table 2. Lipoproteins as assayed by size exclusion chromatography were also unaffected by genotype.

TABLE 2

Fasting Glucose and Insulin Values.

| Parameter | Glucose (mg/dl) | | Insulin (pg/ml) | |
| --- | --- | --- | --- | --- |
| | Baseline | 8 weeks | Baseline | 8 weeks |
| ATM$^{+/+}$ | 157.4 ± 12 | 211.2 ± 13* | 940 ± 200 | 1750 ± 700$^{\#}$ |
| ATM$^{+/-}$ | 178.0 ± 12 | 222.0 ± 12$^{\#}$ | 1870 ± 400 | 2840 ± 500 |
| ATM$^{-/-}$ | 180.1 ± 12 | 236.8 ± 29 | 1590 ± 200 | 2110 ± 900 |

Data are presented as mean ± s.e.m. for >5 apoE$^{-/-}$ animals per ATM genotype. Differences between glucose levels in this table and those in glucose tolerance tests are explained in part by different assays (chemical determinations using serum samples in this table vs. glucose monitor determination using whole blood in glucose tolerance tests) and different periods of fasting (4 hr. in this table vs. 12 hr. for glucose tolerance tests). P values indicate comparisons of values at baseline vs. 8 weeks of high fat-feeding.
*P < 0.001,
$^{\#}$P < 0.05.

However, atherosclerosis assayed by the en face technique (according to Semenkovich et al., J. Lipid Res., 1998, 39: 1141-1151) after 8 weeks on the Western diet was increased in ATM-deficient mice in a manner that was inversely related to gene dosage. At the arch, lesions were about 2-fold greater in ATM$^{+/-}$ and about 3-folder greater in ATM$^{-/-}$ as compared to ATM$^{+/+}$ mice. Relative differences were similar in the abdominal aorta and more pronounced in the thoracic aorta. These results illustrate that atherosclerosis is increased in ATM-deficient mice.

Insulin Signaling Pathways in Mutant Mice

To investigate the accelerated atherosclerosis observed in the ATM deficient mice with systemic insulin resistance and other features of metabolic syndrome, the insulin signaling pathways in the aortas of apoE$^{-/-}$ mice were studied. The protein kinase Akt is known to mediate the metabolic effects of insulin in many tissues, and defective Akt activity is common in insulin resistance. Phospho-Akt, the activated form of this kinase, was decreased in a gene dosage-dependent manner in the aortas of ATM-deficient mice (in the apoE null model). Phospho-Akt activity was lowest in ATM$^{-/-}$ vessels, intermediate in ATM$^{+/-}$, and highest in wild type mice. Similar decreases with ATM deficiency were seen for Phospho-ERK, a MAP kinase family member that usually responds to mitogens, and phospho-p38, a related kinase usually stimulated by stress, while total p38 mass was unaffected by genotype. These results were obtained using aortas isolated from 8 week old mice eating chow and subjected to Western blotting.

Downstream events in insulin signaling such as Akt activation can be blocked by covalent modification of insulin receptor substrates such as phosphorylation at serine 307 of IRS-1. Aortic tissue from ATM$^{-/-}$ mice had the highest level of IRS-1 Ser 307 phosphorylation, ATM$^{+/-}$ aortas were intermediate, and ATM$^{+/+}$ vessels exhibited the lowest amount of IRS-1 Ser 307 phosphorylation in the apoE null mouse model. These data are consistent with the presence of vascular insulin resistance in atherosclerosis-prone ATM-deficient mice due in part to disruption of normal insulin signaling by a specific serine phosphorylation of IRS-1.

The stress-related kinase JNK is known to mediate insulin resistance in part by phosphorylating IRS-1 at serine 307. JNK was activated in the aortas of ATM-deficient mice in proportion to the degree of ATM deficiency. Aortic phospho-JNK in chow fed mice of various ATM genotypes in the ApoE null model was measured by western blot.

Western blotting was performed by standard techniques using antibodies purchased from Cell Signaling (Beverly, Mass.): total Akt, phosphoAkt (Ser472 and Thr308), total p38 and phospho-p38 (Thr180/Tyr182), phospho-ERK (Thr202/Tyr204), total JNK, phospho-JNK (Thr183/Tyr185), total c-Jun, phospho-c-Jun (Ser63), total p53 and phospho-p53 (Ser18). Anti-HSC70 which was purchased from Santa Cruz Biotechnology (Santa Cruz, Calif.). Anti-IRS-2 was purchased from Upstate Biotechnology (Lake Placid, N.Y.). Smooth muscle cells were assayed using a cell-based ELISA kit for phospho-JNK from Activemotif (Carlsbad, Calif.). Thioglycolate-elicited macrophages were assayed using a phospho-JNK ELISA from Sigma (St. Louis, Mo.). Insulin and adiponectin were assayed by ELISA using commercial reagents (Crystal Chem, Downers Grove, Ill. and Alpco Diagnostics, Salem, N.H.).

Insulin Signaling

IRS-2-associated PI 3-kinase activity was determined by immunoprecipitating IRS-2 from post-clamp liver protein extracts using an anti-IRS-2 antibody (Upstate Biotechnology) and assessing PI 3-kinase activity of the IRS-2-containing complex using an ELISA based assay (Echelon Biosciences Inc.). Total and Ser473-phosphorylated Akt levels in whole-cell protein extracts from mice after hyperinsulinemic clamp studies were measured by immunoblotting using antibodies from Cell Signaling. For some studies, mice were fasted overnight, injected with human insulin (10 mU/g), sacrificed 5 min later, then tissues dissected and snap frozen.

Hyperinsulinemic-Euglycemic Clamps

Clamp experiments were performed as described (Bernal-Mizrachi et al., 2003; Nat. Med. 9:1069-1075; Tordjman et al., 2001; J. Clin. Invest. 107:1025-1034). Double lumen catheters were placed and 3-[$^3$H] glucose was infused to steady state. Regular human insulin was infused at 10 mU/kg/min with 25% D-glucose to maintain blood glucose at 120 mg/dl for at least 90 minutes. The 3-[$^3$H]glucose infusion was continued during the clamp with labeled glucose included in the 25% D-glucose infusion to match blood specific activity at steady state. The rate of appearance of glucose ($R_a$), equal to glucose utilization ($R_d$) at steady state, was determined by dividing the infusion rate of labeled glucose by specific activity. Endogenous glucose production was calculated by subtracting the cold glucose infusion rate from the clamp $R_d$.

Most of the mass of the aorta is composed of smooth muscle cells. Smooth muscle cells were cultured from the aortas of apoE$^{-/-}$ mice by the explant technique as described by Weng et al., Proc. Natl. Acad. Sci. USA, 2003, 100:6730-6735. Smooth muscle cells growing from the explants were passaged, expanded, and their identity verified by staining with a fluorescent smooth muscle α-actin antibody (Vector Laboratories, Burlingame, Calif.). Morpholino antisense oligonucleotides directed against mouse ATM and a control were made by Gene Tools (Philomath, Oreg.). The lissamine-tagged antisense oligonucleotide against ATM had the following sequence: 5'-GTGCTAGACTCATGGTTTAA-GATTT-3' (SEQ ID NO:6). Subconfluent mouse primary aortic smooth muscle cells were seeded at a concentration of $1 \times 10^6$ per well in a 6-well tissue culture plate. After culture in serum-reduced DMEM (0.4% FBS) overnight, cells were incubated in a 5-mL solution containing 1.4 μmol/L antisense ATM oligo or control oligo with 0.56 μmol/L ethoxylated polyethylenimine for 3 hours and subsequently switched to normal growth medium for at least 24 hours. Successful transfection was confirmed by fluorescence microscopy and phospho-JNK and total JNK were assayed 72 hours later using a cell-based ELISA kit.

When cultured aortic smooth muscle cells from ATM$^{+/+}$ apoE$^{-/-}$ mice were treated with a Morpholino antisense oligonucleotide to ATM (anti-ATM), JNK activity was increased, as shown by ELISA. Control oligos had no effect on JNK activity. These data show that interference with ATM expression induces JNK activity, a mediator of insulin resistance and atherosclerosis, and JNK activity would serve as a good target to modulate in order to prevent or treat the symptoms associated with metabolic syndrome (including insulin resistance and/or atherosclerosis).

Macrophages are often involved in initiating early atherosclerotic lesions, and the presence of JNK in macrophages is proatherogenic. Total JNK activity was increased in thioglycolate-elicited macrophages from ATM-deficient mice. Expression of IRS-2, the predominant insulin receptor substrate in macrophages, was decreased in ATM-deficient cells, indicating impaired insulin signaling.

For LPL assays, cells were fed on day 6. On day 7, cells were washed and incubated in DMEM plus 0.5% BSA for 4 hr, followed by incubation with 10 U/ml heparin, collection of media, and subsequent determination of LPL activity as described (Coleman et al., 1995; J. Biol. Chem. 270:12518-12525). For JNK inhibition studies, cells were incubated in cell culture medium for 15 hr in the presence of a JNK-specific inhibitor (SP600125, Sigma, St. Louis, Mo.) or vehicle (DMSO). Cells were further incubated for 1 hr in DMEM plus 0.5% BSA plus SP600125 or vehicle in 10 U/ml heparin, then media were assayed.

IRS-2 message levels were determined using total RNA (1 μg) that was treated with DNase and reverse transcribed using Superscript II (Invitrogen, Carlsbad, Calif.) and oligo-dT as primer. PCR was performed with the GeneAmp® 7000 Sequence Detection System using the TaqMan® Universal Master reagent kit (Applied Biosystems, Foster City, Calif.). A negative control using RNA not subjected to reverse transcription was included in each assay.

Mouse IRS-2 was detected with the follow primer/probe set: forward primer 5'-CAGTCCCACATCAGGCTTGAG-3' (SEQ ID NO:7), reverse 5'-GGACTGCACGGATGACCT-TAG-3' (SEQ ID NO:8), labeled probe with 5'-carboxyfluorescein (FAM) and carboxytetramethylrhodamine (TAMRA) 5'FAM-CCTTCAAGTCAGCCAGCCCCCTG-TAMRA-3' (SEQ ID NO:9); mouse LPL forward: 5'-TTC ACT TTT CTG GGA CTG AGA ATG-3' (SEQ ID NO:10), reverse 5'-GCC ACT GTG CCG TAC AGA GA-3' (SEQ ID NO:1), probe 5'-FAM-TCC AGC CAG GAT GCA ACA-TAMRA-3' (SEQ ID NO:12), mouse EGR-1: forward 5'-GCC TCG TGA GCA TGA CCA AT-3' (SEQ ID NO:13), reverse 5' GCA GAG GAA GAC GAT GAA GCA-3' (SEQ ID NO:14), probe 5'-FAM-CTC CGA CCT CTT CAT CCT CGG CG-BH-3' (SEQ ID NO: 15). Sequence-specific amplification was detected with an increasing fluorescence signal of FAM (reporter dye) during the amplification cycle. Co-amplification of the mRNA for the rodent GAPDH control reagent (Applied Biosystems, Foster City, Calif.) or mouse ribosomal protein L32 (forward 5'-AAGCGAAACTGGCGGAAAC-3' (SEQ ID NO:16), reverse 5'-GATCTGGCCCTTGAACC-3' (SEQ ID NO:17), probe 5'-HEX-CAGAGGCATTGACAA-CAGGGTGCG-BH-3' (SEQ ID NO:18)) was performed in the same tube for all samples. All assays were run in triplicate. The results are expressed as relative expression of mRNA normalized to GAPDH or L32 levels that were not affected by genotype. A VIC TaqMan® murine GAPDH control reagent (Applied Biosystems, Foster City, Calif.) was used to normalize results. GAPDH was not affected by genotype.

The comparative $C_T$ method was employed for quantification. JNK increases AP-1 activity, and AP-1 is known to increase the expression of lipoprotein lipase, which is known to be proatherogenic in macrophages. LPL enzyme activity was increased in ATM-deficient macrophages, providing one likely mechanism for the increased diet-induced atherosclerosis in ATM deficiency.

Blood Pressure Determinations

Systolic and diastolic blood pressures were measured over several days in conscious mice using a tail-cuff system (Kent Scientific, Litchfield, Conn.) as described (Bernal-Mizrachi et al., 2003; Nat. Med. 9:1069-1075). Animals were habituated to the blood pressure apparatus for several days before data were collected. Five to eight measurements were recorded for each mouse at each of three daily sessions. Results are presented as the mean of those measurements on consecutive days.

These results demonstrate that ATM deficiency is a potential cause of, or is at least associated with the metabolic syndrome, resulting in insulin resistance and increased atherosclerosis. ATM deficiency increases JNK activity, which impairs glucose tolerance by interfering with insulin signaling through serine 307 phosphorylation of IRS-1 and promotes atherosclerosis by increasing macrophage LPL activity through AP-1. Macrophage JNK activity is gauged by assaying activated JNK1 and 2 (pThr$^{183}$/pTyr$^{185}$) by ELISA (Sigma, St. Louis) according to the manufacturer's instructions. Briefly, lipoprotein lipase (LPL) enzyme activity is determined by measuring the release of labeled fatty acids from a triolein emulsion in macrophages. Cells were fed on day 6. On day 7, cells were washed and incubated in DMEM plu 0.5% BSA for 4 hours, followed by incubation with 10 U/ml heparin, collection of media, and subsequent determination of LPL activity as described by Coleman et al., J. Biol. Chem., 1995, 270:12518-12525. Macrophages from the same sources were used in the assays.

Reduction of Vascular Disease with Low-Dose Chloroquine Treatment in ATM Deficient Mice Since deficiency of ATM can cause vascular disease, modulating or increasing ATM activity represents a novel approach for treating vascular dysfunction. The inventors have been able to show that providing chloroquine at low concentrations activates ATM in cultured cells. Chloroquine dose-response experiments were performed in mice using a variety of endpoints including phosphorylation of p53 as a surrogate marker of ATM activation. Using activated p53 as a marker is preferred, since it is a more sensitive measure of ATM activity. However, low level activation of ATM as detected with an antibody that recognizes serine phosphorylation at residue 1981, may also be used in the assay. Effects on p53 activation and the vascular phenotype were observed after using 3.5 mg/kg of chloroquine (a low dose) administered by intraperitoneal injection twice a week (a total weekly dose of 7.0 mg/kg).

$ATM^{+/+}$ $apoE^{-/-}$ mice (of both sexes on a chow diet) at the age of 8 weeks were treated with either chloroquine diphosphate (Sigma, St. Louis, Mo.) dissolved in 0.9% saline or saline alone administered at 7 mg/kg body weight per week after a loading dose of 7 mg/kg. The mice were then fed the Western-type diet as described. Body composition was performed on anaesthetized, living mice by dual energy X-ray absorptiometry (PIXImus, GE Corporation). Chloroquine had no effect on body weight or metabolic rate (measured by indirect calorimetry). However, after 8 weeks, glucose tolerance was improved compared to saline-treated mice. These results demonstrate that low dose chloroquine improves glucose tolerance in high fat-fed mice.

p53 is antiatherogenic and activated in diseased vessels, such as those in patients with metabolic syndrome. Detection of activated p53 phosphorylated at serine residue 18 is a robust marker of ATM activation. Chloroquine treatment increased p53 activation in the aortas of mice on Western diet, consistent with ATM activation by the drug. The results show increased activated p53 in the aortic tissue of mice treated with chloroquine (CHQ, 7 mg/kg/week) as compared to saline injected mice.

Activation of the ATM-p53 axis by low dose chloroquine had no effect on serum lipids, including fasting serum cholesterol, triglycerides and non-esterified fatty acids (NEFA), determined at baseline for mice on a chow diet without drug treatment and following 4 and 8 weeks of Western diet feeding with chloroquine (7 mg/kg/week) or saline injections. All of these experiments were performed using $ATM^{+/+}$ $apoE^{-/-}$ littermate mice beginning at the age of 8 weeks.

Serum is generally obtained after a four hour fast and assayed for routine chemistries (glucose, triglycerides, cholesterol, and non-esterified fatty acids) using an automated plate reader connected to a computer, as described by Li et al., Nat. Med., 2000, 6:1115-1120. Insulin assays are performed on 5 μl of serum by ELISA (Crystal Chem., Chicago). For measurement of lipoproteins, serum from multiple animals will be pooled and separated using superose columns. Additional aliquots of serum are frozen for subsequent determination of leptin, adiponectin, etc., if appropriate.

Chloroquine treatment decreased atherosclerosis by 37% at the arch, 25% at the thoracic aorta, and 25% at the abdominal aorta. Atherosclerosis was assayed by using the en face technique on the same mice, following 8 weeks of Western diet feeding with chloroquine (CHQ) or saline treatment. This experiment was performed with 25 animals in the chloroquine group and 21 animals in the saline group. Equal numbers of males and females were studied; chloroquine was effective in both genders.

Thus, the ATM-dependence of the chloroquine effect has been demonstrated in several ways. First, a group of $ATM^{-/-}$ $apoE^{-/-}$ mice and a group of $ATM^{+/+}$ $apoE^{-/-}$ mice were randomized to saline treatment or chloroquine injections (7 mg/kg/week, as described above) and fed the Western diet for 8 weeks. As expected, systolic and diastolic blood pressures were increased in the ATM-deficient mice. Chronic (long-term, or extended) low dose chloroquine treatment significantly lowered systolic pressure by 9 mm Hg in $ATM^{+/+}$ mice, as compared to saline treated $ATM^{+/+}$ mice. There was a similar trend for diastolic blood pressure in these animals with functional ATM. There was no effect of chloroquine in the ATM-deficient animals.

Additional evidence of the ATM-dependence of the chloroquine effect, was shown in isolated peritoneal macrophages from $ATM^{+/+}apoE^{-/-}$ and $ATM^{-/-}apoE^{-/-}$ mice that were treated chronically for six weeks with low dose chloroquine in the setting of the Western diet. Macrophages were isolated as described by Febbraio et al., J. Clin. Invest., 2000, 105: 1049-1056. The mice were injected intraperitoneally with a 4% solution of thioglycolate media (Sigma, St. Louis, Mo.) on day 1. On day 5, peritoneal macrophages were isolated, washed, counted, and plated in DMEM plus 10% FBS. Macrophages were subsequently harvested at various times to isolate RNA or protein, respectively, according to standard methods.

As compared to saline-treated mice, chloroquine significantly decreased phospho-JNK activity in macrophages from $ATM^{+/+}$ mice, but had no effect in ATM null macrophages. The results measured total phospho-JNK activity in thioglycolate-elicited peritoneal macrophages from $ATM^{+/+}apoE^{-/-}$ and $ATM^{-/-}apoE^{-/-}$ mice treated with chloroquine (CHQ, 7 mg/kg/week) or saline after 6 weeks on Western diet. The percentage difference in activated JNK for macrophages from CHQ-treated was compared to saline-treated mice. These results suggest that the vascular effects of chloroquine are ATM-dependent and are at least partially mediated by suppression of JNK activity, a known contributor to insulin resistance and lesion development.

To further illustrate that the chloroquine effect is dependent on the presence of ATM, Western diet-fed $ATM^{-/-}apoE^{-/-}$ mice were treated with saline or chloroquine at a dose of 7 mg/kg/week for 8 weeks and assaying for atherosclerosis using the en face technique. The quantification of aortic lesions involved cleaning the aortas and pinning them on a wax matrix with the intimal surface facing upward (en face). Images were captured with a digital camera, edited for artifacts, and data were reported as the percent involvement of the arch (encompassing the surface from the aortic valve to the left subclavian artery), thoracic aorta (extending to the last intercostal artery), and abdominal aorta (to the ileal bifurcation). At the time of isolation, hearts were embedded in optical coherence tomography (OCT) media and frozen to permit quantification of lesion formation by staining of serial cryostat-cut sections of the aortic sinus, if necessary. These samples were also used for immunocytochemistry.

Bone Marrow Transplantation

Marrow was isolated from the femurs and tibias of 8-10 week old $ATM^{+/+}apoE^{-/-}$ and $ATM^{-/-}apoE^{-/-}$ mice by flushing the bones with cold PBS. Total bone marrow was washed, triturated using a 24 gauge needle (Benson Dickson, Franklin Lakes, N.J.), collected by centrifugation at 1250 rpm for 4 min and diluted with PBS. After lysis of erythrocytes using 0.05% sodium azide, cells were counted to obtain a defined concentration of unfractionated bone marrow. Recipient mice were lethally irradiated with 10 Gy from a cesium 137 gamma cell irradiator. Within 6 hours after irradiation, recipients were reconstituted with ~$5 \times 10^6$ donor marrow cells via a single injection. The donor marrow was allowed to repopulate for 4 weeks after the transplantation. The resultant null allele was detected by genotyping of DNA from blood (Qiagen Blood Kit, Germantown, Md.). For estimating engraftment, total bone marrow was isolated from the femurs and tibias from C57BL/6-TgN(ACThEGFP) (GFP) mice that were crossed onto an apoE null background. The marrow was processed as described and ~5×10⁶ cells of unfractionated bone marrow in PBS were injected into a cohort of apoE null mice in parallel to those described above. Four weeks later, blood was drawn from the recipient mice, from GFP apoE null mice and from non-irradiated apoE null mice. The degree of engraftment as assessed by FACS quantification of the percentage of GFP in peripheral leucocytes as compared to non-transplanted controls and the transgenic donor mice was 66-92%. Recipient mice were then placed on a Western-type diet for 8 weeks followed by measurement of serum chemistries and determination of atherosclerosis lesion extent by the aortic origin technique.

ATM-Deficient Bone Marrow-Derived Cells Increase Atherosclerosis

Since macrophages initiate early atherosclerotic lesions, $ATM^{+/+}apoE^{-/-}$ mice were transplanted with bone marrow from $ATM^{+/+}apoE^{-/-}$ or $ATM^{-/-}apoE^{-/-}$ animals. After four weeks of recovery (and verification of engraftment), animals were started on the Western diet, then lesions were quantified by lipid staining of the aortic origin 8 weeks later. Lesions were 80% larger in animals transplanted with ATM null marrow There was no marrow genotype effect on fasting cholesterol (1,110±69 mg/dl for $ATM^{+/+}$ vs. 1,183±74 mg/dl for $ATM^{-/-}$), glucose or triglycerides. ATM deficiency was associated with increased JNK activity and increased phosphorylation of c-Jun in $ATM^{-/-}$ macrophages. JNK, by increasing activity of the transcription factor AP-1, increases expression of early growth response gene-1 (Egr-1) and lipoprotein lipase (LPL). mRNA levels for both Egr-1 and LPL (data were expressed relative to L32 expression) were increased several-fold in ATM null macrophages from transplanted mice. Macrophages isolated from littermate mice not subjected to transplantation also had increased JNK activity and LPL enzyme activity with ATM deficiency.

Since JNK appears to be involved in the vascular disease of ATM deficiency, it should be induced with Western diet feeding in apoE null mice. Western diet-fed but not chow-fed apoE null mice (wild type at the ATM locus) showed a robust increase in activated aortic JNK. Phosphorylated ATM is difficult to detect in mouse tissues, but detection is straightforward for p53, a major substrate of activated ATM. Activated p53 (phospho-p53(Ser18)) was also detected in the aortas of Western diet-fed but not chow-fed apoE null mice, consistent with ATM activation. This finding could reflect a protective response to limit vascular disease or implicate the ATM-p53 axis in atherogenesis.

Reduction of Metabolic Abnormalities with the ATM-Activating Drug Chloroquine

To determine if promoting ATM activity decreases vascular dysfunction, we treated mice with the anti-malarial drug chloroquine, which activates ATM in cultured cells. Administration of low dose chloroquine (determined in dose response experiments) to mice resulted in p53 activation in fat and muscle as well as liver, aorta and cultured macrophages. ATM+/+apoE−/− mice were randomized to treatment with saline injections or 3.5 mg/kg of chloroquine administered by intraperitoneal injection twice a week (a total weekly dose of 7.0 mg/kg) and fed a Western diet. After eight weeks, chloroquine had no effect on body weight or metabolic rate determined by indirect calorimetry. Animals were treated with intraperitoneal injections of chloroquine at 3.5 mg/kg per injection or the same volume of saline as control. Western blots showed phospho-p53 in fat and muscle.

Activation of the ATM-p53 axis by low dose chloroquine also had no effect on serum lipids, but decreased atherosclerosis. Animals were treated with twice-weekly intraperitoneal injections of chloroquine at 3.5 mg/kg per injection for a total weekly dose of 7.0 mg/kg. Fasting serum lipids at baseline on chow diet and following Western diet feeding for 4 and 8 weeks in CHQ- and saline-treated mice. Lesion area was 37% less at the arch, 25% less at the thoracic aorta, and 25% less at the abdominal aorta in chloroquine-treated mice. Equal numbers of males and females were studied and chloroquine was effective in both genders, Chloroquine also improved metabolic abnormalities in established models of insulin resistance. At the same dose that decreased atherosclerosis in apoE null mice, chloroquine lowered both fasting and fed glucose levels as well as fasting insulin levels (13,360±1996 pg/ml for chloroquine vs. 16,810±1,120 for saline, P<0.05) in ob/ob mice and fed glucose levels in db/db mice. Fasting blood glucose with CHQ were lower compared to baseline and compared to the vehicle (saline) controls 3 weeks after initiation of the treatment. Fed blood glucose levels on two different days were lower as compared to baseline and lower than the saline-treated controls. Saline-treated controls did not differ from baseline in the fasting or fed state. Blood glucose in male db/db mice were treated with either CHQ or saline. Baseline represents the average fed blood glucose levels of the 12 db/db mice. CHQ treated db/db mice had lower blood glucose levels as compared to the baseline and as compared to the saline-treated controls on two different days of the treatment period. The saline-treated animals did not differ from baseline.

ATM deficiency also affected glucose metabolism in mouse models without apoE deficiency. In aged (>1 year old) littermate low density lipoprotein receptor (LDLR) mice, heterozygous ATM deficiency resulted in impaired glucose tolerance and resistance to glucose lowering by insulin. Western diet feeding of $ATM^{+/-}$ and littermate $ATM^{+/+}$ mice in a wild type C57BL/6 background also produced greater glucose intolerance in the ATM heterozygotes. The intraperitoneal glucose tolerance testing was conducted on 12 aged $ATM^{+/+}$ and 11 aged $ATM^{+/-}$ (>1 year of age) littermate mice on the LDLR null background eating a chow diet. The intraperitoneal insulin tolerance test (ITT) was also conducted on these mice. The intraperitoneal glucose tolerance testing was also conducted for 8 $ATM^{+/+}$ and 8 $ATM^{+/-}$ littermate mice on a C57BL/6 background after 4 weeks on Western diet. These data suggest that increasing ATM activity in models other apoE null mice decreases insulin resistance.

Several lines of evidence were pursued to investigate the ATM-dependence of the chloroquine effect. In vivo chloroquine treatment decreased LPL enzyme activity (for mice treated systemically with chloroquine, compared to saline treated animals with P<0.05) and phospho-JNK activity (for mice treated systemically with chloroquine, compared to saline treated animals with P<0.01) in peritoneal macrophages from $ATM^{+/+}$ mice but had no effect in ATM null macrophages. Chloroquine treatment lowered systolic pressure by 9 mm Hg in $ATM^{+/+}$ mice as compared to saline-treated $ATM^{+/+}$ mice.

There was no effect of chloroquine in the ATM-deficient animals. Chloroquine improved glucose tolerance in Western diet-fed $ATM^{+/+}apoE^{-/-}$ mice but not $ATM^{-/-}apoE^{-/-}$ mice. The glycemic response in the ATM null mice was atypical, showing a late drop in glucose levels that could reflect abnormally delayed release of insulin. $ATM^{+/+}$ pancreatic islets manifested a prominent induction of ATM expression with lipid loading, suggesting a role for ATM in beta cell homeostasis. Taken together, these data suggest that several of the effects of chloroquine in this model are ATM-dependent.

Since JNK is the proposed link between ATM and its downstream effects, we inhibited JNK activity in elicited macrophages (using the compound SP600125) and assayed LPL enzyme activity. Elevated LPL activity in ATM null cells was decreased to control levels with JNK inhibition. Increased LPL activity was also reduced to control levels with SP600125 treatment in ATM$^{+/-}$ macrophages. LPL enzyme activity of thioglycollate-elicited macrophages obtained from ATM$^{+/+}$ and ATM$^{-/-}$ mice (n=3 for each) that were treated in culture with a JNK inhibitor (SP600125) or vehicle (DMSO). These results are consistent with a role for JNK in the mediation of some of the effects induced by ATM deficiency in this model.

Statistical Analyses

Statistical significance of differences was calculated using: the Student unpaired t test for parametric data involving two groups, ANOVA for parametric data usually with Dunnett's or Bonferroni post tests, the Mann-Whitney test for non-parametric data involving two groups, and the Kruskal-Wallis test for non-parametric data with Dunn's post test.

Example 2

Human Studies

Subjects meeting the ATP III criteria for the metabolic syndrome have been enrolled and will continue to be enrolled in a study consisting of four limbs to test whether the administration of low dose and very low dose chloroquine to humans activates the ATM-p53 axis and leads to an improvement in the symptoms of metabolic syndrome.

Subjects between the age of 18 and 55 meet the ATP III criteria for the metabolic syndrome and do not have retinal abnormalities, G6PD deficiency, or certain other major active medical conditions, as described in more detail below. Each has at least three of the following five characteristics: elevated fasting triglycerides (greater than or equal to about 150 mg/dl), low HDL cholesterol (less than about 50 mg/dl in women, less than about 40 mg/dl in men), hypertension (blood pressure greater than or equal to about 130/85 mm Hg), increased waist circumference (greater than about 35 inches in women, greater than about 40 inches in men) and elevated fasting glucose (greater than or equal to about 100 mg/dl). If an individual takes one of the antihypertensive agents recommended by JNC 7 for hypertension, this is accepted as meeting the blood pressure requirement even if the measured blood pressure is below about 130/85. Enrollment is open to children (those between the ages of 18 and 21), males and females, and members of all racial and ethnic groups. Participants are screened in two stages.

First, potential subjects are interviewed, the protocol is be explained in detail, then risks and benefits of involvement are discussed. Interested subjects have a complete history and physical examination (including several measurements of blood pressure according to a standard protocol and determination of waist size, both performed by experienced personnel in the Washington University GCRC, St. Louis, Mo.). Fasting blood sugar and fasting serum lipids are measured. Individuals with the following criteria are excluded: prior travel to countries requiring malarial prophylaxis or prior known treatment with chloroquine or hydroxychloroquine, morbid obesity (BMI greater than or equal to about 45), coronary artery disease, peripheral artery disease (including carotid disease), history of stroke, chronic renal insufficiency, diabetes, seizure disorder, psoriasis (chloroquine has been reported to cause exacerbations of this disease through unclear mechanisms), hematologic disorders, current malignancies, asthma or other active respiratory disease, liver disease, active infections, or any other serious ongoing illness (including alcohol or drug abuse) requiring medical care. Pregnant women or those trying to become pregnant are also excluded.

Individuals taking any prescription medications are excluded (including lipid lowering medications) with the exception of antihypertensive agents in men and women and oral contraceptives in women. In terms of antihypertensive agents, individuals taking stable doses of any single medication currently recommended by JNC 7 as appropriate initial therapy may be enrolled. Those taking more than one agent and those with uncontrolled hypertension (defined for this study as having blood pressure greater than or equal to about 160/100) will be excluded. Participants are asked not to take over-the-counter medications during the study, with the exception of acetaminophen for minor pain. They are specifically instructed to avoid cimetidine (which is known to increase chloroquine levels) and vitamin E (which may decrease chloroquine uptake by cells).

Second, those meeting the entrance criteria undergo the following tests: CMP (including liver function tests and creatinine), CBC, TSH, a test for glucose-6-phosphate deydrogenase, EKG, hearing test, and a complete opthalmology evaluation including visual field testing and slit lamp examination. Provided all of these results are normal and informed consent is obtained, subjects begin the protocol as described.

Using a factor of $\frac{1}{12}$ for converting doses expressed in mg/kg in mice to an equivalent surface area dose expressed in mg/kg for humans (described by Freireich et al., Cancer Chemother. Rep., 1966, 50:219-244) corresponds to a dosage of about 40 mg per week in a 70 kg human, or about 80 mg per week in a 120 kg human. The calculation, based on the 7 mg/kg/week dosage used in mice with features of metabolic syndrome to reverse atherosclerosis and diminish symptoms of metabolic syndrome is: 120 kg×7 mg/kg/week[mouse dose] divided by 12 [correction factor for surface area] divided by 0.9 [correction for oral absorption] equals about 78 mg. Since the results with 80 mg/day in humans have been surprisingly good, even lower doses such as 80 mg/week or the equivalent are being tested.

Enrolled subjects with the metabolic syndrome are treated with a placebo for three weeks for limb 1, oral chloroquine at 80 mg/day (8% of the dose used in previous studies to define the metabolic effects of chloroquine) for three weeks for limb 2, oral chloroquine at 80 mg/week for three weeks for limb 3, and chloroquine at 250 mg/day (25% of the dose used in previous metabolic studies) for three weeks for limb 4. At the end of each treatment period, participants have measurements of fasting serum lipids, glucose tolerance testing, a variety of other serum measurements including chemistries and markers of vascular disease, undergo ambulatory blood pressure monitoring, and insulin resistance is quantified by means of the hyperinsulinemic-euglycemic clamp procedure. Glucose and insulin tolerance tests are generally performed using D-glucose (1 g/kg) and insulin (0.75 U/kg), which are administered in separate procedures followed by serial measurements of blood glucose. If necessary, an oral glucose tolerance test (OGTT) will be performed the day after completing the clamp. After an overnight fast, an intravenous catheter will be placed, baseline labs will be obtained, 75 g of glucose will be consumed, and blood glucose, insulin, C peptide, and glucagon will be determined every half hour for 2 hours.

Two subjects with the metabolic syndrome have completed the protocol. The mean glucose infusion rate to maintain euglycemia (90 mg/dl) at steady state during the first stage of the clamp (using an insulin infusion rate of 15 mU/m$^2$/min) for these two subjects was determined. Chloroquine at a dose of 80 mg per day resulted in a 63% increase in glucose infusion rate to maintain the blood glucose, indicating a substantial increase in insulin sensitivity. This 63% increase was a surprising result considering the low dose of chloroquine administered. (Previous studies using high chloroquine doses of 1000 mg/day for three days detected only a 13% increase in the glucose infusion rate required to maintain euglycemia in patients with type 2 diabetes.) Individual responses were nearly identical for each subject. Glucose infusion rates were appropriately higher for the euglycemia second stage of the clamp (insulin at 40 mU/m$^2$/min in each limb), with 80 mg dose of chloroquine increasing the glucose infusion rate by 23% compared to the placebo, and the 250 mg dose having a blunted effect, the same pattern seen for the first stage of the clamps.

Clamps are performed with infusion of stable isotope-labeled glucose to allow the determination of both glucose disposal rates and hepatic glucose output during hyperinsulinemic-euglycemic clamps in subjects with the metabolic syndrome. The results are presented as the mean for two subjects. Baseline glucose disposal (in the absence of insulin infusion) under these conditions was undetectable. Low dose chloroquine in these human subjects with the metabolic syndrome had an insulin sensitizing effect on both peripheral tissues and the liver. Chloroquine at the low dose of 80 mg/day increased glucose disposal in peripheral tissues by 62%, a surprisingly high amount, and decreased hepatic glucose production by 58% during the first stage of the clamp.

Fasting lipids and lipoproteins in subjects with the metabolic syndrome were determined after 3 weeks of treatment with placebo, chloroquine 80 mg/day, or chloroquine 250 mg/day. Data are the average of two subjects in mg/dl.

Chloroquine also had beneficial effects on fasting lipids in these two subjects with metabolic syndrome. Chloroquine at 80 mg/day for three weeks was associated with a 25% decrease in LDL cholesterol, a 17% decrease in total cholesterol and a 10% decrease in triglycerides (as shown in Table 3), Ambulatory blood pressures (systolic, diastolic, mean arterial for the entire study period and for the 6 am to midnight and midnight to 6 am periods) did not appear to be affected in these two subjects. Glucose tolerance tests were also unaffected. Body weight and diet did not change during this protocol.

TABLE 3

|  | Placebo | CHQ 80 | CHQ 250 |
|---|---|---|---|
| Total Cholesterol | 206 | 172 | 169 |
| LDL cholesterol | 132 | 100 | 99 |
| HDL cholesterol | 47 | 47 | 51 |
| Triglycerides | 139 | 125 | 129 |

Monocyte/macrophages were also successfully isolated from these subjects during each limb of the protocol. Anticoagulated blood was added to commercially available tubes containing Histopaque, and mononuclear cells were collected after centrifugation. These cells were subjected to a brief second spin using a discontinuous sucrose gradient to remove platelets (which can interfere with the adherence of monocytes to culture dishes), then the mononuclear cells were placed in tissue culture dishes. Two hours later, lymphocytes were washed away, and adherent monocytes were collected and frozen in appropriate media so that cells from different limbs of the protocol can subsequently be studied in the same assays. Chloroquine treatment resulted in activation of ATM and p53 in monocytes, the cell type responsible for the initiation of atherosclerotic lesions. These western blots showed activated ATM and activated p53 in monocytes from the same subject following either three weeks of 80 mg/day chloroquine or three weeks of 250 mg/day chloroquine. The western blots showed no activation of ATM or p53 in monocytes isolated from a subject receiving placebo. For activated ATM determinations, lysates were immunoprecipitated using a total ATM antibody (D1611). The immunoprecipitated samples were blotted for activated ATM using a monoclonal antibody recognizing Ser1981P-ATM. The gels included a positive control of 293 cells treated with camptothecin. Total lysates were used to blot activated p53 using a polyclonal antibody to Ser15P-p53 (cell signaling). To confirm the p53 data, total lysates were tested using an ELISA-based p53 DNA binding assay (TransAM p53 activity assay from Active Motif). These results showed a near-linear increase in p53 binding to the consensus binding site with increasing chloroquine dose. The same results were also seen using monocytes from another subject.

The pattern for ATM mirrored that for insulin sensitivity, with greater activation at the low 80 mg/day dose and a blunted effect at the higher 250 mg/day dose. For p53, activation was directly related to the chloroquine dose. Using the same lysates, phopho-JNK activity (by ELISA) was decreased by chloroquine in a dose-dependent fashion.

These data show that ATM deficiency promotes metabolic syndrome and vascular disease in a mouse model, and low dose chloroquine treatment in the mouse model decreases vascular disease and has metabolic effects (including suppression of JNK activity) that are ATM-dependent, and low dose chloroquine in humans improves insulin sensitivity and dyslipidemia. The effects in humans appear to be associated with activation of ATM and p53 in monocytes as well as decreased JNK activity.

Long Term Studies

These data show that administration of low dose chloroquine in mice decreases atherosclerosis, lowers blood pressure and improves glucose intolerance and suggests that analogous administration of low dose chloroquine in humans (80 mg/day) improves insulin sensitivity and dyslipidemia. A randomized, parallel group, placebo-controlled study of the effect of chloroquine in human subjects with the metabolic syndrome is ongoing to determine whether chronic or prolonged low dose chloroquine treatment also decreases vascular disease in people with the metabolic syndrome. In the active treatment group for this study, the total chloroquine dose is 29 grams (assuming complete compliance).

Retinal toxicity is known to be a problem associated with chronic chloroquine therapy. It is believed that the lowest cumulative dose associated with this side effect is about 125 grams. In the active treatment groups for the present study, the total cumulative chloroquine dose is proposed to be 29 grams (assuming complete compliance). Additionally, every participant undergoes baseline eye exams and repeat exams at 6 and 12 months. Plasma chloroquine levels are also monitored during the active treatment portion of the study and at the 24 month time point.

A consideration for prolonged treatment is that chloroquine remains in tissues for a long time. Beneficial effects of the drug may persist after discontinuation of treatment. To address this issue, subjects from both the placebo and chloroquine arms of the human study will stop taking capsules at 12 months but return at 24 months for carotid IMT, OGTT and blood draws. If enhanced insulin sensitivity and less carotid progression are seen in the chloroquine group, this observation could provide the foundation for intermittent, very low dose chloroquine as an appropriate treatment for the metabolic syndrome.

SUMMARY

Metabolic syndrome is a common disorder associated with insulin resistance and atherosclerosis. The present data show that deficiency of one or two alleles of ATM, the protein mutated in the cancer-prone disorder ataxia telangiectasia, worsens features of the metabolic syndrome and accelerates atherosclerosis in Western diet-fed apoE−/− mice. Hyperinsulinemic-euglycemic clamps showed these animals to have hepatic insulin resistance. Atherosclerosis was greater when animals were transplanted with ATM−/− as compared to ATM+/+ marrow, consistent with a role for marrow-derived cells such as macrophages in ATM-deficient vascular disease. Jun N-terminal kinase (JNK) activity was increased in ATM-deficient cells including macrophages. Treatment of ATM+/+apoE−/− mice with low dose chloroquine, an ATM activator, decreased atherosclerosis. In an ATM-dependent manner, chloroquine decreased macrophage JNK activity, decreased macrophage lipoprotein lipase activity (a proatherogenic consequence of JNK activation), decreased blood pressure, and improved glucose tolerance. Chloroquine also improved metabolic abnormalities in ob/ob and db/db mice. These results suggest that ATM-dependent stress pathways mediate susceptibility to the metabolic syndrome and that chloroquine or related agents promoting ATM activity could represent a novel approach for modulating insulin resistance and decreasing vascular disease.

Discussion

Metabolic syndrome is common and potentially lethal. Treatment is limited to therapies for the disparate components of the syndrome: hypertension, hyperglycemia, obesity, and dyslipidemia. The current data demonstrate that apoE null mice with ATM haploinsufficiency have accelerated features of the metabolic syndrome. They are insulin resistant with increased JNK activity. Treatment of ATM+/+ mice in the apoE null background with low doses of the ATM-activating drug chloroquine lowers blood pressure, improves glucose tolerance, suppresses JNK activity, and decreases diet-induced atherosclerosis. Chloroquine also improves metabolic abnormalities in ob/ob and db/db mice. Collectively, these findings suggest that modulation of ATM-dependent signaling with chloroquine represents a potential treatment for the metabolic syndrome.

Cholesterol levels were modestly higher in ATM+/−apoE−/− as compared to ATM+/+apoE−/− mice in the current study on a chow diet at baseline but this difference was not significant, and the inventors did not detect significant genotype effects on serum cholesterol at subsequent time points (3 and 8 weeks) in mice fed a Western diet. These results suggest that in the setting of a Western diet, events independent of differences in cholesterol promote atherogenesis in ATM deficiency.

ATM has been linked to insulin signaling in certain cell types and it has been suggested that individuals heterozygous for ATM deficiency are prone to cardiovascular disease. No mechanistic insights have existed to explain these associations. The current data link ATM and signaling pathways known to affect atherogenesis and responses to insulin and elucidates novel mechanisms for these pathways. JNK is an attractive potential mediator of the metabolic effects caused by ATM deficiency. Activated JNK phosphorylates cJun, which combines with cFos to form the AP-1 transcription factor complex. Activation of both JNK and the AP-1 pathway are present in the brains of ATM-deficient mice. JNK activity is linked to several features of the metabolic syndrome. JNK activity is increased by endoplasmic reticulum stress caused by obesity. Mice deficient in JNK1, one of three isoforms, are protected from obesity and insulin resistance. Expressing wild type JNK decreases insulin sensitivity in liver, while expressing dominant negative JNK increases insulin sensitivity in liver. JNK decreases the expression of adiponectin, which has insulin sensitizing effects, in adipocyte cell lines. Treatment of animals with a JNK inhibitor enhances insulin sensitivity. JNK interferes with insulin signaling by phosphorylating serine residue 307 on IRS-1. Inhibition of JNK activity and genetic JNK2 deficiency in apoE null mice decreases atherosclerosis.

The present data show that genetic deficiency of ATM increases JNK activity in multiple tissues, and is associated with systemic insulin resistance, serine 307 phosphorylation of IRS-1, and accelerated atherosclerosis. Disruption of ATM expression in cultured cells induces JNK, and transplantation of mice with ATM-deficient marrow increases atherosclerosis in the setting of macrophages with increased JNK activity. JNK induces Egr-1 and LPL and both were increased in ATM-deficient macrophages. Egr-1 has been shown to promote atherosclerosis in apoE null mice and a proatherogenic role for LPL in macrophages has been demonstrated, thus providing a mechanism for increased atherosclerosis. Treatment with chloroquine suppresses JNK activity and LPL activity in macrophages from ATM+/+ but not ATM−/− mice, and increased LPL activity in ATM-deficient macrophages is normalized by JNK inhibition, suggesting that ATM-dependent suppression of JNK mediates susceptibility to metabolic effects. Thus, atherosclerosis, insulin resistance, and the component clinical features of the metabolic syndrome may share a common unifying mechanism related to ATM deficiency.

ATM signals to the p53 tumor suppressor gene product. Interestingly, p53 has been reported to reduce atherogenesis in mouse models, to inactivate JNK, and to mediate an antioxidant function, potentially relevant to ATM and the metabolic syndrome. Markers of oxidative stress are increased in mice and humans with ATM deficiency and inhibition of oxidative stress pathways decreases reactive oxygen species and improves metabolic syndrome in obese mice.

The present inventors explored the relationship between ATM and metabolic syndrome in part because the loss of ATM worsens metabolic parameters in apoE null mice, and the inventors previously found that chloroquine can activate the ATM kinase (Bakkenist and Kastan, 2003). The linking and testing of these observations allowed the present inventors to demonstrate the ATM-dependence of many of the metabolic effects of chloroquine, a dependence not previously suspected.

In summary, ATM deficiency is a novel mechanism contributing to development of the metabolic syndrome. The present results provide evidence that modulating ATM-dependent signaling with low doses of chloroquine, comparable to ~40 mg/week in a 70 kg human, reduces vascular disease.

All of the compositions and methods disclosed and claimed herein can be made and executed without undue experimentation in light of the present disclosure. While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

All publications and patent applications mentioned in this specification are herein incorporated by reference to the same extent as if each individual publication or patent application was specifically and individually indicated to be incorporated by reference.

What is claimed is:

1. A method for increasing Ataxia-Telangiectasia Mutated (ATM) protein kinase activity in a mammal with metabolic syndrome, which method comprises administering an effective amount of a chloroquine compound to a mammal in need of such treatment, wherein the chloroquine compound (i) enhances the activity of ATM kinase in the mammal and (ii) is selected from the group consisting of mefloquine, pyronaridine, piperaquine, amodiaquine, and quinidine, enantiomers thereof, pharmaceutically acceptable salts thereof, and mixtures thereof, or has a structure of Formula I:

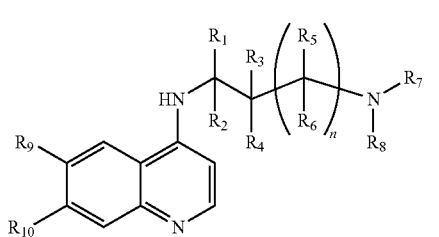

wherein
$R_1$ to $R_6$ are independently selected from hydrogen or alkyl, provided that no more than two substituents from $R_1$ to $R_6$ may be simultaneously alkyl; $R_7$ and $R_8$ is hydrogen, alkyl, alkenyl or aralkyl, or together with the N atom signify pyrrolidine or piperidine, which optionally can be substituted by alkyl, or octahydroindole or 3-azabicyclo[3,2,2]nonane; $R_9$ is hydrogen or halogen; $R_{10}$ is halogen or trifluoromethyl; and
n =0 or 1; or
wherein the symbols $R_1$ and $R_3$ is tri- or tetramethylene; $R_2$ and $R_4$ to $R_6$ is hydrogen;
n =0; and $R_7$ and $R_8$ are defined as above; or
wherein the symbols $R_1$ and $R_7$ is methylene or dimethylene and n=1, or
$R_1$ and $R_7$ are di- or trimethylene and n =0, or
$R_3$ and $R_7$ are di- or trimethylene and n =1, or
$R_3$ and $R_7$ are tri- or tetramethylene and n =0, or
$R_5$ and $R_7$ are tri- or tetramethylene and n =1, or
$R_1$ and $R_5$ are di- or tri-methylene and n =1, and
the remaining substituents are hydrogen, except $R_8$ which is alkyl, alkenyl or alkynyl;
wherein the symbols $R_3$ and $R_5$ is tri- or tetramethylene and n =1; all remaining substituents to $R^6$ are hydrogen; and $R^7$ and $R^8$ are alkyl, alkenyl or aralkyl or together with the N atom are pyrrolidine or piperidine, which optionally can be substituted by alkyl; $R_9$ is hydrogen or halogen; and $R_{10}$ is halogen or trifluoromethyl,
enantiomers thereof, pharmaceutically acceptable salts thereof, and mixtures thereof.

2. The method of claim 1, wherein the effective amount of chloroquine compound ranges from between about 0.6 mg/kg/day to about 3 mg/kg/day.

3. The method of claim 1, wherein the mammal exhibits improvement in symptoms associated with metabolic syndrome when compared to symptoms prior to administering said effective amount of the chloroquine compound.

4. The method of claim 3, wherein the effective amount of the chloroquine compound ranges from about 0.6 mg/kg/day to about 3 mg/kg/day.

5. The method of claim 1, wherein the metabolic syndrome comprises at least three symptoms selected from the group consisting of elevated fasting triglycerides (greater than or equal to 150 mg/dl), low HDL cholesterol (less than 50 mg/dl in women, less than 40 mg/dl in men), hypertension (blood pressure greater than or equal to 130/85 mm Hg), increased waist circumference (greater than 35 inches in women, greater than 40 inches in men) and elevated fasting glucose (greater than or equal to 100 mg/dl).

6. The method of claim 5, wherein the mammal exhibits improvement in symptoms associated with the metabolic syndrome when compared to symptoms prior to administering an effective amount of a chloroquine compound.

7. The method of claim 1, wherein the chloroquine compound is at least one compound selected from the group consisting of chloroquine, chloroquine phosphate, hydroxychloroquine, chloroquine diphosphate, chloroquine sulphate, hydroxychloroquine sulphate, enantiomers thereof, pharmaceutically acceptable salts thereof, and mixtures thereof.

8. The method of claim 7 wherein the compound is chloroquine.

9. The method of claim 7 wherein the compound is hydroxychloroquine.

10. The method of claim 8 or 9 wherein the compound is an essentially pure (+) isomer.

11. The method of claim 8 or 9 wherein the compound is an essentially pure (-) isomer.

12. The method of claim 8 or 9 wherein the compound is a mixture of isomers.

13. The method of claim 1 or 3 wherein the amount of the compound administered is at least about 0.1 mg/kg/day.

14. The method of claim 1 wherein the amount of the compound administered ranges from about 0.8 mg/kg/day to about 1.2 mg/kg/day.

15. The method of claim 1 wherein the amount of the compound administered ranges from about 3.5 mg kg/week to about 7 mg/kg/week.

16. The method of claim 1 wherein the amount of the compound administered ranges from about 0.1 mg/kg/day to about 0.2 mg/kg/day.

17. The method of claim 1 wherein the amount of the compound administered is about 80 mg/day.

18. The method of claim 1, which comprises administering the chloroquine compound more than once a week.

19. The method claim 1, which comprises administering the chloroquine compound daily.

20. The method of claim 1, which comprises administering the chloroquine compound every two weeks.

21. The method of claim 1, which comprises administering the chloroquine compound once a month.

22. The method of claim 1 wherein the chloroquine compound is formulated in a sustained release formulation.

23. The method of claim 1 wherein the amount of the compound administered ranges from about 0.1 mg/kg to about 9 mg/kg once a week.

24. A method of delaying the onset or reducing the severity of metabolic syndrome in a mammal, which method comprises administering to a mammal at risk of metabolic syndrome, an effective amount of a chloroquine compound, wherein the chloroquine compound (i) enhances the activity of Ataxia-Telangiectasia Mutated (ATM) kinase in the mammal and (ii) is selected from the group consisting of mefloquine, pyronaridine, piperaquine, amodiaquine, and quinidine, enantiomers thereof, pharmaceutically acceptable salts thereof, and mixtures thereof, or has a structure selected from the group consisting of Formula I:

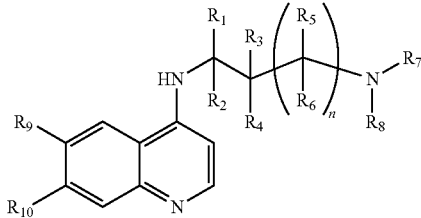

wherein $R_1$ to $R_6$ are independently selected from hydrogen or alkyl, provided that no more than two substituents from $R_1$ to $R_6$ may be simultaneously alkyl; $R_7$ and $R_8$ is hydrogen, alkyl, alkenyl or aralkyl, or together with the N atom signify pyrrolidine or piperidine, which optionally can be substituted by alkyl, or octahydroindole or 3-azabicyclo[3,2,2]nonane; $R_9$ is hydrogen or halogen; $R_{10}$ is halogen or trifluoromethyl; and n = 0 or 1; or wherein the symbols $R_1$ and $R_3$ is tri- or tetramethylene; $R_2$ and $R_4$ to $R_6$ is hydrogen;

n = 0; and $R_7$ and $R_8$ are defined as above; or wherein the symbols $R_1$ and $R_7$ is methylene or dimethylene and n=1, or $R_1$ and $R_7$ are di- or trimethylene and n = 0, or $R_3$ and $R_7$ are di- or trimethylene and n = 1, or $R_3$ and $R_7$ are tri- or tetramethylene and n = 0, or $R_5$ and $R_7$ are tri- or tetramethylene and n = 1, or $R_1$ and $R_5$ are di- or tri-methylene and n = 1, and the remaining substituents are hydrogen, except $R_8$ which is alkyl, alkenyl or alkynyl;

wherein the symbols $R_3$ and $R_5$ is tri- or tetramethylene and n = 1; all remaining substituents to $R^6$ are hydrogen; and $R^7$ and $R^8$ are alkyl, alkenyl or aralkyl or together with the N atom are pyrrolidine or piperidine, which optionally can be substituted by alkyl; $R_9$ is hydrogen or halogen; and $R_{10}$ is halogen or trifluoromethyl, enantiomers thereof, pharmaceutically acceptable salts thereof, and mixtures thereof.

25. The method of claim 1 or 24, wherein the mammal has been free of malaria for at least one year before commencing administration of the chloroquine compound.

26. The method of claim 25, wherein the mammal has never suffered from malaria before commencing administration of the chloroquine compound.

27. The method of claim 1 or 24, wherein the mammal is free of psoriasis, malaria, protozoal infections, Epstein Barr virus infection, Alzheimer's disease, Parkinson's disease, lupus erythematosus, rheumatism, hypercalcemia, multiple sclerosis, and migraine.

28. The method of claim 1 or 24 which method further comprises administering an effective amount of at least a second pharmaceutically active compound.

29. The method of claim 28, wherein the second pharmaceutically active compound is selected from the group consisting of an antihyperglycemic diabetes treatment, an antihypertensive agent, an antithrombotic agent, and an inhibitor of cholesterol synthesis or absorption.

* * * * *

UNITED STATES PATENT AND TRADEMARK OFFICE
CERTIFICATE OF CORRECTION

PATENT NO. : 8,440,695 B2  
APPLICATION NO. : 12/093198  
DATED : May 14, 2013  
INVENTOR(S) : Michael B. Kastan, Clay F. Semenkovich and Jochen Schneider Page 1 of 1

It is certified that error appears in the above-identified patent and that said Letters Patent is hereby corrected as shown below:

In the Claims  
Column 63, Line 48 - In Claim 1, delete "$R^6$" and insert --$R_6$--  
Column 63, Line 49 - In Claim 1, delete "$R^7$ and $R^8$" and insert --$R_7$ and $R_8$--  
Column 66, Line 6 - In Claim 24, delete "$R^6$" and insert --$R_6$--  
Column 66, Line 7 - In Claim 24, delete "$R^7$ and $R^8$" and insert --$R_7$ and $R_8$--

Signed and Sealed this  
Seventeenth Day of September, 2013

Teresa Stanek Rea  
*Deputy Director of the United States Patent and Trademark Office*